(12) United States Patent
Tanaka et al.

(10) Patent No.: US 10,575,738 B2
(45) Date of Patent: Mar. 3, 2020

(54) MAGNETIC FIELD MEASUREMENT APPARATUS AND METHOD FOR NOISE ENVIRONMENT

(71) Applicant: ADVANTEST CORPORATION, Tokyo (JP)

(72) Inventors: Takeshi Tanaka, Tokyo (JP); Yuji Ogata, Tokyo (JP); Yoshiyuki Hata, Tokyo (JP); Toshiaki Hayakawa, Tokyo (JP); Tomoaki Ueda, Kyoto (JP)

(73) Assignee: ADVANTEST COPORATION, Tokyo (JP)

( * ) Notice: Subject to any disclaimer, the term of this patent is extended or adjusted under 35 U.S.C. 154(b) by 60 days.

(21) Appl. No.: 15/645,433

(22) Filed: Jul. 10, 2017

(65) Prior Publication Data

US 2018/0014738 A1    Jan. 18, 2018

(30) Foreign Application Priority Data

Jul. 13, 2016 (JP) .................. 2016-138447

(51) Int. Cl.
*A61B 5/04* (2006.01)
*A61B 5/00* (2006.01)
*G01R 33/00* (2006.01)
*A61B 5/0265* (2006.01)
*A61B 5/024* (2006.01)
*G01F 1/56* (2006.01)
*G01R 15/14* (2006.01)
(Continued)

(52) U.S. Cl.
CPC .......... *A61B 5/04005* (2013.01); *A61B 5/024* (2013.01); *A61B 5/0265* (2013.01); *A61B 5/02444* (2013.01); *A61B 5/7203* (2013.01); *G01F 1/56* (2013.01); *G01R 15/148* (2013.01); *G01R 33/0076* (2013.01); *G01R 33/022* (2013.01); *A61B 5/18* (2013.01); *A61B 5/7225* (2013.01); *A61B 5/7246* (2013.01); *A61B 2562/0223* (2013.01); *A61B 2562/046* (2013.01)

(58) Field of Classification Search
CPC ...................................................... G01R 29/26
See application file for complete search history.

(56) References Cited

U.S. PATENT DOCUMENTS

| 4,969,469 A | * | 11/1990 | Mills | ...................... | G01R 33/16 324/201 |
| 5,073,858 A | * | 12/1991 | Mills | ...................... | G01R 33/16 324/201 |

(Continued)

FOREIGN PATENT DOCUMENTS

| JP | H05-15504 | 1/1993 |
| JP | 2004-172151 | 6/2004 |

(Continued)

*Primary Examiner* — Noam Reisner

(57) ABSTRACT

In a magnetic field measurement apparatus and a magnetic field measurement method provided herein, a magnetic field from an object is measured by a magnetic sensor group including a plurality of magnetic sensors. Then, an estimated value of a common noise component included in observed quantities of the magnetic sensors of all the channels of the magnetic sensor group is obtained as an external magnetic noise component. Finally the magnetic signal from the object is calculated by subtracting the estimated value from the observed quantity of each of the magnetic sensors.

21 Claims, 26 Drawing Sheets

(51) Int. Cl.
*G01R 33/022* (2006.01)
*A61B 5/18* (2006.01)

(56) References Cited

U.S. PATENT DOCUMENTS

| | | |
|---|---|---|
| 2007/0205736 A1* | 9/2007 | Lindberg ............ G01D 5/24452 318/490 |
| 2012/0197145 A1 | 8/2012 | Wu et al. |
| 2012/0219195 A1 | 8/2012 | Wu et al. |
| 2013/0079622 A1 | 3/2013 | Wu et al. |
| 2014/0077612 A1 | 3/2014 | Onuma et al. |
| 2015/0069846 A1 | 3/2015 | Hokari |
| 2016/0305999 A1* | 10/2016 | Li ......................... G01R 29/26 |

FOREIGN PATENT DOCUMENTS

| | | |
|---|---|---|
| JP | 2005-217341 | 8/2005 |
| JP | 2005-227245 | 8/2005 |

\* cited by examiner

A : S/N ∝ $\frac{1}{\sqrt{2}}$

B : S/N ∝ $\frac{1}{\sqrt{9}}$

MAGNETIC FIELD MEASUREMENT APPARATUS AND METHOD FOR NOISE ENVIRONMENT

CROSS-REFERENCE TO RELATED APPLICATIONS

This application is based upon and claims the benefit of priority of the prior Japanese Patent Application No. 2016-138447, filed on Jul. 13, 2016, the entire contents of which are incorporated herein by reference.

TECHNICAL FIELD

The present invention relates to a magnetic field measurement apparatus and method.

BACKGROUND OF THE INVENTION

Magnetic signals produced from a living body include, for example, a cardiac magnetic field accompanying movement of the cardiac muscles of the heart and a brain magnetic field generated by neurotransmission of the brain. The magnetic field produced from such a living body is extremely weak, and the cardiac magnetic field is at 1 to 100 pico-Tesla whereas the cerebral magnetic field is at 10 to 1000 femto-Tesla.

On the other hand, there are magnetic noise components such as geomagnetism and a magnetic field from a power line, which are as large as several tens of micro-Tesla and larger than magnetic signals produced from the living body. Therefore, in order to detect a magnetic signal from a living body, it is important to remove a magnetic noise component.

As a method of measuring a weak magnetic signal produced from a living body, a method using a gradiometer has been proposed.

In the gradiometer, a measurement sensor for measuring a magnetic signal from a living body and a reference sensor for detecting an external magnetic field entering from the outside are used in pair. Of these sensors, the measurement sensor is placed close to the living body, and the reference sensor is disposed at a distance of about 5 cm to 10 cm from the measurement sensor.

Then, the measurement of a magnetic signal from the living body includes subtracting the magnetic field detected by the reference sensor as a noise component from the magnetic field detected by the measurement sensor.

In the measurement for an object, the object is placed in a magnetic shield chamber covered with a material having a large magnetic permeability such as permalloy, thereby preventing an external magnetic field from intruding.

CITATION LIST

Patent Documents

[Patent Document 1] Japanese Unexamined Patent Publication No. 2016-006817
[Patent Document 2] Japanese Unexamined Patent Publication No. 2004-172151
[Patent Document 3] Japanese Unexamined Patent Publication No. 2005-217341

SUMMARY OF THE INVENTION

Problem to be Solved by Invention

The conventional gradiometer only calculates a simple difference between the reference sensor and the measurement sensor. For this reason, in a place where there are influences of various magnetic field noise components, the noise reduction rate is not sufficient, and therefore it is difficult to measure a weak magnetic field such as a magnetic signal from the living body.

Also, having a large and heavy structure due to the necessity to perform measurement in the magnetic shield chamber made of permalloy or the like, the gradiometer is difficult to carry and operate outdoors.

Furthermore, since it is necessary to dispose the reference sensor at a distance from the surface of an object such as a living body, it is difficult to apply a gradiometer to a thin type wearable sensor for use in close contact with the object such as the living body.

An objective of the present invention is to provide a magnetic field measurement apparatus and a magnetic field measurement method which can measure a weak magnetic signal while achieving downsizing of the apparatus. Note that weak magnetic signals in the present invention are not limited to signals from a living body.

Means for Solving the Problem

According to one aspect of the present invention, there is provided a magnetic field measurement apparatus comprising: a magnetic sensor group including a plurality of magnetic sensors, an average value calculating unit configured to calculate a common noise component commonly applied to observed quantities of the magnetic sensors of all channels of the magnetic sensor group, and a noise removing unit configured to detect a magnetic field from the object by subtracting the common noise component obtained by the average value calculating unit as an estimated value of a magnetic noise component from the observed quantity of each of the magnetic sensors.

According to the another aspect of the present invention, there is provided a magnetic field measurement method comprising the steps of: obtaining observed quantities from a plurality of magnetic sensors arranged near an object; calculating a common noise component commonly applied to observed quantities of the magnetic sensors of all the channels; detecting a magnetic field from the object by subtracting the common noise component from the observed quantity of each of the magnetic sensors.

According to the magnetic field measurement apparatus and the magnetic field measurement method of the above aspects, it is possible to measure a weak magnetic field, for example, a signal from a living body, without using a magnetic shield chamber, and the apparatus configuration can be reduced in size.

DESCRIPTION OF EMBODIMENTS

First Embodiment

Figure 1:
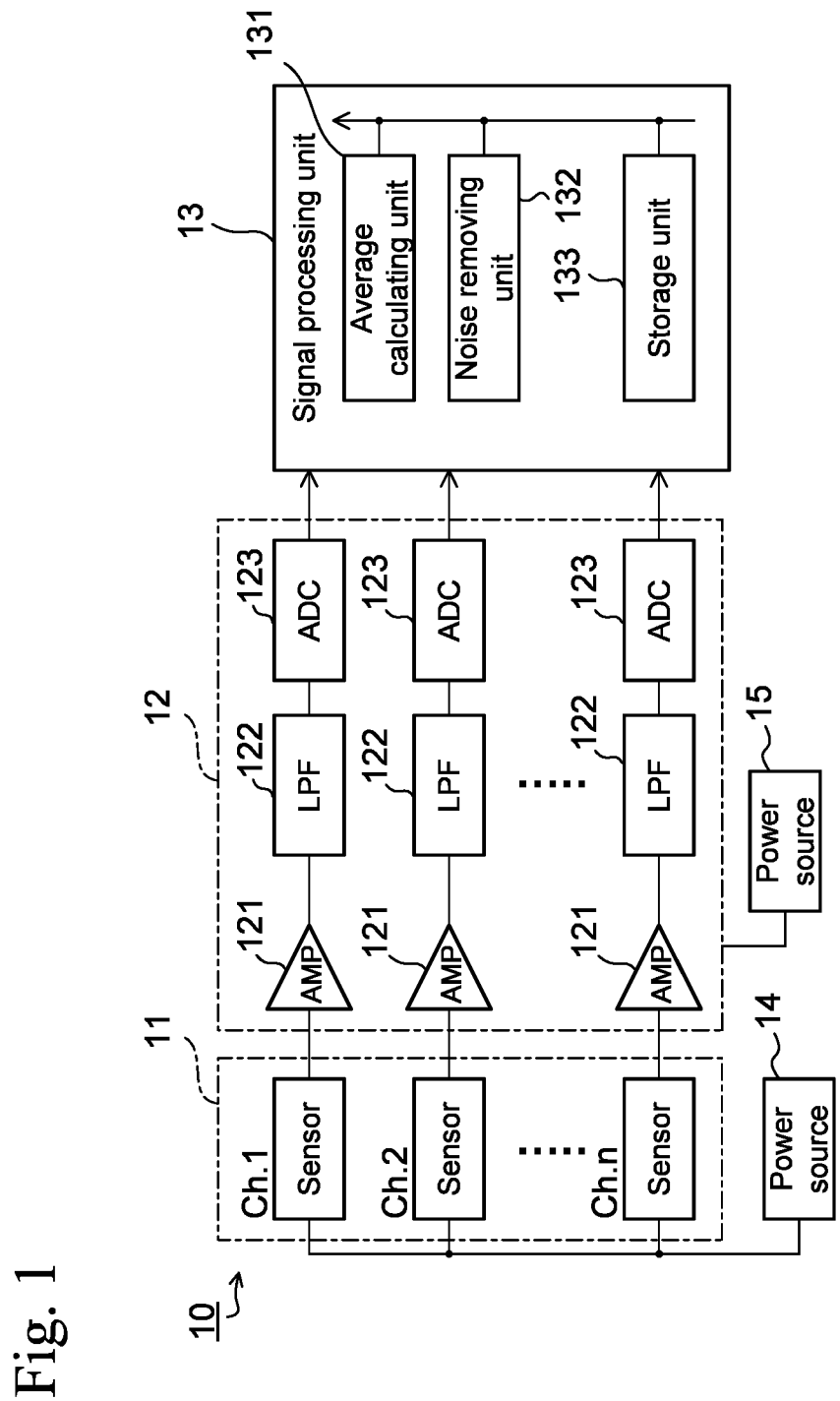
FIG. 1 is a block diagram of a magnetic field measurement apparatus according to a first embodiment.
Figure 2:
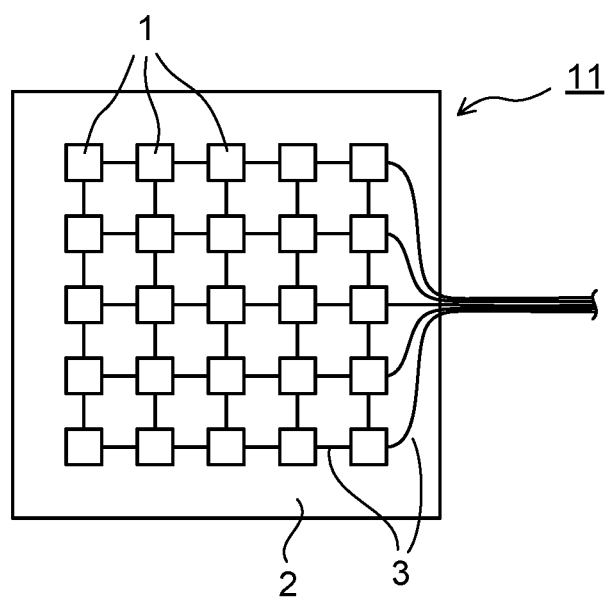
FIG. 2 is a plan view illustrating the structure of a magnetic sensor group of the magnetic field measurement apparatus of FIG. 1.

FIG. 1 is a block diagram of a magnetic field measurement apparatus 10 according to the present embodiment, and FIG. 2 is a plan view illustrating a structure of a magnetic sensor group 11 of the magnetic field measurement apparatus of FIG. 1.

As illustrated in FIG. 1, the magnetic field measurement apparatus 10 of the present embodiment comprises a magnetic sensor group 11 which including a plurality of magnetic sensors 1.

As illustrated in FIG. 2, the magnetic sensor group 11 has the plurality of magnetic sensors 1 arranged in an array pattern with fixed pitches in the row direction and the column direction. The magnetic sensors 1 are fixed on a flexible support member 2.

A wiring 3 is connected to each magnetic sensor 1. The wiring 3 supplies a current to the magnetic sensor 1 and transmits a detection signal of the magnetic sensor 1.

The size of the magnetic sensor group 11 is, for example, 20 cm in length and width for the purpose of measuring the magnetic field of the heart. In this case, the number of the magnetic sensors 1 is, for example, 64 in total of 8 rows×8 columns.

Preferably, the size of the magnetic sensor group 11 may be larger than a measurement object. More preferably, the size of the magnetic sensor group 11 may be set to such a size that the magnetic sensor group 11 can cover at least a part of the measurement object. In this case, the number of magnetic flux lines produced from the measurement object and passing through the magnetic sensor group 11 and the number of magnetic flux lines passing through the magnetic sensor group 11 and returning to the measurement object are approximately the same. The magnetic sensor group 11 arranged in this manner can achieve conditions suitable for noise removal as described later.

As the magnetic sensor 1 included in the magnetic sensor group 11, various magnetic sensors such as a magneto-impedance element (MI element), a magneto-resistance element (MR element), a giant magneto-resistance element (GMR element), and a Hall element can be used. The sensitivity of the magnetic sensor 1 is set as appropriate depending on a measurement object. For example, the sensitivity is set to the pico-Tesla order so as to detect a magnetic field in pico-Tesla order produced from a motion of the cardiac muscles, and is set to the femto-Tesla order so as to detect a very-weak magnetic field in femto-Tesla order produced from the transmission of the brain nerve signals.

These magnetic sensors 1 included in the magnetic sensor group 11 are disposed on the flexible support member 2. Thereby, the magnetic sensor group 11 can be deformed along the surface of the living body. On the support member 2, the wirings 3 are provided in a lattice pattern, and the magnetic sensor 1 is disposed at each intersection.

The arrangement of the magnetic sensors 1 is not limited to the intersections of the rectangular lattice. Instead, the magnetic sensors 1 may be arranged on nodes of a triangular or hexagonal mesh structure, or be disposed in portions other than the nodes of the mesh structure. The magnetic sensor 1 may be arranged so as to be randomly distributed on the support member 2.

As illustrated in FIG. 1, the magnetic sensors 1 in the magnetic sensor group 11 are connected in parallel. A common power supply circuit 14 is connected to the magnetic sensors 1, and the magnetic sensors 1 are operated by a current from the common power supply circuit 14. This is because the noise of the power supply circuit 14 is superimposed as a common component on signals of the magnetic sensors 1 and the common component can be easily removed.

Detection signals of the magnetic sensors 1 are input to an input circuit 12. The input circuit 12 includes an amplifier circuit 121 provided for each magnetic sensor 1.

The signal of the magnetic sensor 1 is amplified by the amplifier circuit 121 and then input to a low-pass filter 122. Since the magnetic signal from the living body is at 100 Hz or less, a frequency component far exceeding this value is unnecessary for the measurement. Therefore, a high-frequency component (noise) unnecessary for measurement is removed from the detection signal of the magnetic sensor 1 by the low-pass filter 122.

Thereafter, the detection signal of the magnetic sensor 1 is converted into a digital signal by an AD conversion circuit 123 and input to a signal processing unit 13.

The signal processing unit 13 performs noise removal from a detection signal of the magnetic sensor 1 (hereinafter referred to as an observed quantity), and outputs a detection value of a magnetic field from the object (hereinafter referred to as a measured quantity).

The signal processing unit 13 is provided with an average value calculating unit 131, a noise removing unit 132, and a storage unit 133 for performing the noise removal processing.

For the same reason as the power supply circuit 14, a single power supply circuit 15 is also connected to the input circuit 12. The amplifier circuits 121, the low-pass filters 122, and the AD conversion circuits 123 operate by the current from the power supply circuit 15.

Hereinafter, a noise removal method of the magnetic field measurement apparatus 10 of the present embodiment will be described.

Figure 3:
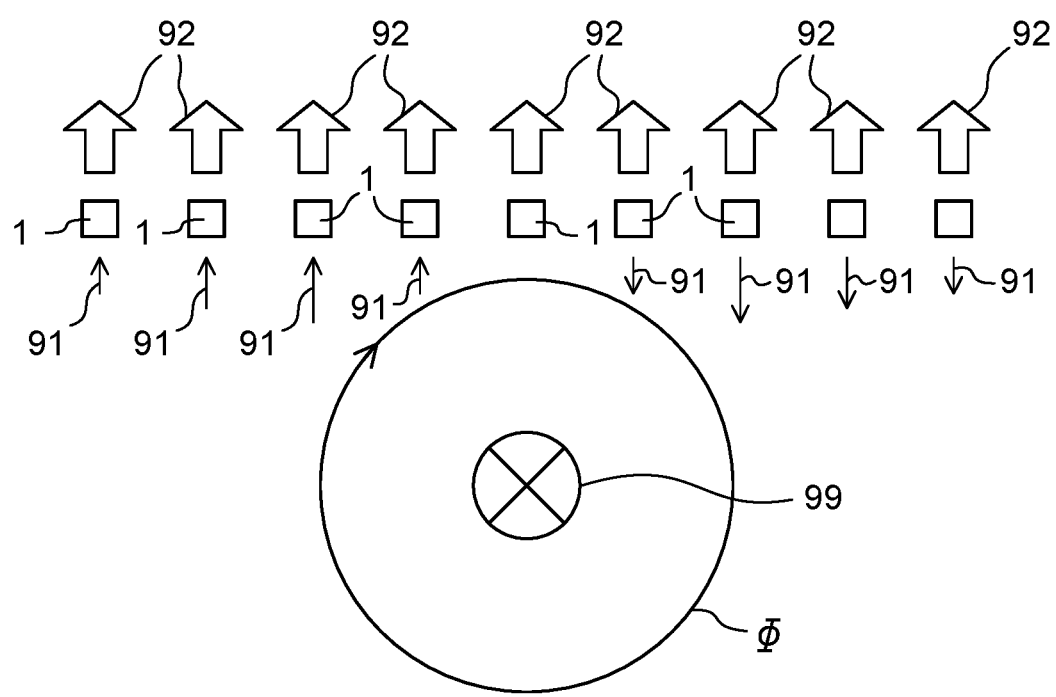
FIG. 3 is a diagram illustrating a magnetic field applied to the magnetic sensor group.

FIG. 3 is a diagram illustrating a magnetic field acting on the magnetic sensors 1.

As shown in FIG. 3, in the present embodiment, the magnetic sensor group 11 is arranged so as to cover at least a part of an object 99.

With such arrangement, some of the magnetic sensors 1 are opposed to the object 99.

Assume that a current flowing toward the back side of the drawing sheet flows into the object 99. In this case, the current flowing through the object 99 generates a magnetic flux, which is indicated by a reference symbol $\varphi$ in FIG. 3, around the object 99.

The magnetic sensors 1 each detect the intensity of a component in the vertical direction in FIG. 3 out of the magnetic flux $\varphi$. The observed quantities of the magnetic field components detected by the magnetic sensors 1 show a distribution as indicated by arrows 91 in FIG. 3.

Since the magnetic sensor group 11 is arranged to cover the object 99, the number of magnetic flux lines crossing the magnetic sensor group 11 upward and the number of magnetic flux lines crossing the magnetic sensor group 11 downward are approximately the same among the magnetic flux lines produced by the object 99 as indicated by the arrows 91 in FIG. 3.

The object 99 is, for example, cardiac muscles that perform a motion of the heart in a living body, and the magnetic flux density applied to the magnetic sensor 1 is on the order of several pico-Tesla to several tens of pico-Tesla.

On the other hand, an AC magnetic field component generated from a commercial power source, surrounding electronic equipment, and the like, and a DC magnetic field component due to geomagnetism are applied as an external magnetic field noise component to the magnetic sensors 1.

Such an external magnetic field noise component occurs at a position distant from the object 99, and has such a large curvature that the external magnetic field noise component acts at substantially equal level over the magnetic sensor group 11, as shown by outline arrows 92 in FIG. 3. In other words, the external magnetic field noise component acts as a common noise component.

Generally, the external magnetic field noise component may take a much larger value than that of the object 99. For example, if the object 99 moves and approaches a steel frame of a building during the measurement, the magnetic field of the steel frame magnetized with geomagnetism may act to apply magnetic noise of several tens of milli-Tesla to the magnetic sensor group 11.

Furthermore, if there is an elevator or a railroad line around the object 99, a magnetic field generated by several thousand amperes of a current flowing in overhead wirings or the line is added as a noise component in addition to the magnetic field from the iron structure.

In the urban environment, magnetic noise from nearby cars and indoor and outdoor electric wirings is also added, and it is extremely difficult to measure the magnetic field from the object 99 such as a living body.

However, these magnetic noise source causes noise at a location distant from the object 99. The magnetic flux from such distant location has a large curvature and the magnetic noise from the magnetic noise source appears as components common to the magnetic sensors 1 of the magnetic sensor group 11.

That is, the density distribution of the magnetic flux crossing the magnetic sensors 1 of the magnetic sensor group 11 tends to be constant.

On the other hand, the magnetic field from the object 99 generates magnetic flux lines confined to a narrow range so as to surround the object 99. Therefore, when the magnetic sensor group 11 is arranged as illustrated in FIG. 3, and when the sum (or the average value) is taken across the observed quantities output from the respective magnetic sensors 1 of the magnetic sensor group 11, the plus components and the minus components of the magnetic flux lines are canceled out each other and their resultant value in the sum (the average value) is substantially zero.

In the present embodiment, an average value of the observed quantities of the magnetic sensors 1 of all the channels is taken. This average value represents the external magnetic noise component. Thereafter, the average value is subtracted from the observed quantity of the magnetic sensor 1 of each channel. As a result, the external magnetic noise component is removed, and the magnetic signal from the object 99 is obtained as the measured quantity.

Figure 4:
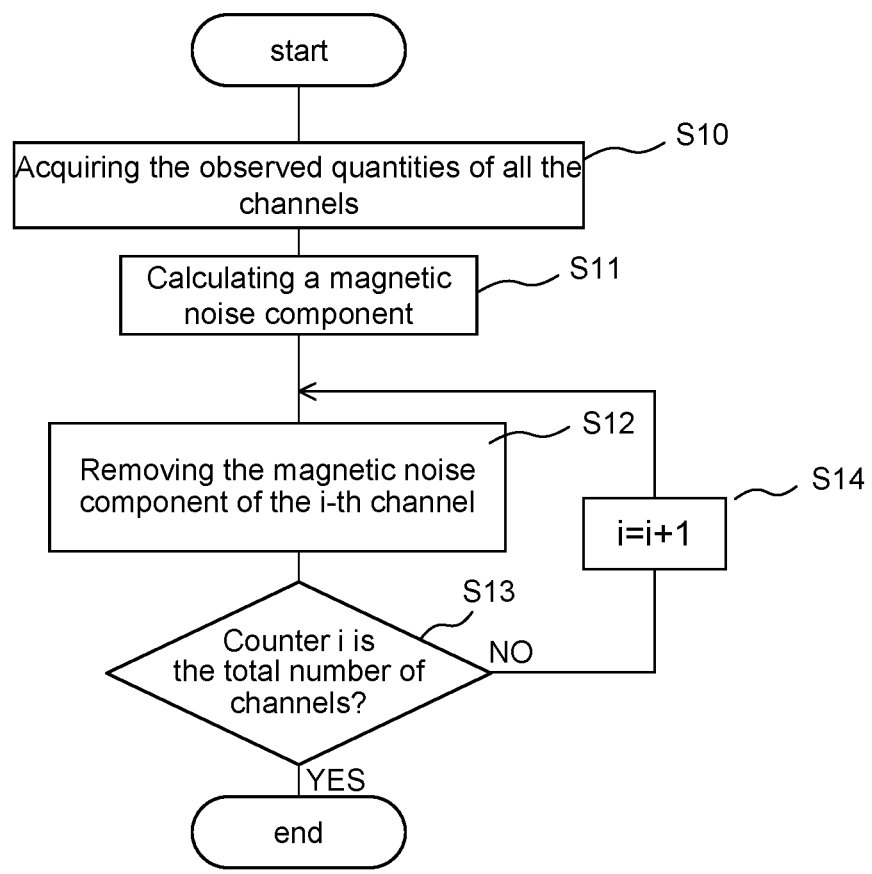
FIG. 4 is a flowchart illustrating the operation of the magnetic field measurement apparatus according to the first embodiment.

FIG. 4 is a flowchart illustrating an operation of the magnetic field measurement apparatus 10 of the present embodiment.

As illustrated in FIG. 4, in step S10, the magnetic field measurement apparatus 10 first acquires the observed quantities of the magnetic sensors 1 of all the channels. Data on the observed quantities of the magnetic sensors 1 is stored in the storage unit 133 of the signal processing unit 13.

Next, in step S11, the signal processing unit 13 calculates a magnetic noise component. In this embodiment, the average value calculating unit 131 of the signal processing unit 13 reads the observed quantities of all the channels from the storage unit 133 and obtains a magnetic noise component by calculating an average of the observed quantities.

In step S12, the noise removing unit 132 reads the observed quantity of the magnetic sensor 1 of the first (i=1) channel from the storage unit 133. Subsequently, the average value calculated in step S11 is subtracted from the read observed quantity to calculate the measured quantity of the first channel.

Note that the measured quantity is a quantity calculated by removing the noise component from the observed quantity of the magnetic sensor 1. The measured quantity represents a magnetic signal from the object 99 at the position of each of the magnetic sensors 1.

Thereafter, in step S13, the signal processing unit 13 determines whether or not noise removal has been completed for all the channels based on the counter i. When the signal processing unit 13 determines in step S13 that noise removal has not been completed for all the channels (NO), the process proceeds to step S14 to increment the counter i by 1, and then returns to step S12.

On the other hand, if the signal processing unit 13 determines in step S13 that noise removal has been completed for all the channels, the process is terminated.

By the processing of steps S11 to S14, the measured quantity of the magnetic component from the object 99 in each magnetic sensor 1 is obtained.

As described above, since the component remaining in the average value of the observed quantities of all the channels is removed as a magnetic noise component, a weak magnetic field from the object 99 can be measured with high sensitivity without using a reference coil. Thereby, the magnetic sensor group 11 can be made thin enough to perform the measurement with the magnetic sensor group 11 attached to a living body.

Second Embodiment

As described with reference to FIG. 3, in the calculated average value of the observed quantities of all the channels of the magnetic sensor group 11, the magnetic components from the object 99 are canceled out each other to become zero, whereas the magnetic noise component mainly remains.

However, noise components generated by the magnetic sensor 1 include shot noise and thermal noise. Shot noise and thermal noise occur randomly in each of the magnetic sensors 1 and have no correlation with those in the other magnetic sensors 1. Hereinafter, a noise component non-correlated among the magnetic sensors 1 is referred to as a non-correlated component. In the calculated average of the observed quantities of the magnetic sensors of all the channels, the non-correlated component is made undistinguishable by the averaging. Therefore, the non-correlated component cannot be removed by the method described in the first embodiment.

Since the magnetic field produced from the living body is very weak, the non-correlated component of each of the magnetic sensors 1 cannot be ignored. The non-correlated component also hinders the detection of the signal by the magnetic field from the living body.

Therefore, it is preferable to remove random non-correlated components occurred in the magnetic sensors 1.

Referring to FIG. 3, magnetic signals from the object 99 appear as in-phase components between the magnetic sensor 1 of interest and the magnetic sensor 1 adjacent to the magnetic sensor 1 in the vicinity thereof. In the present embodiment, the non-correlated component is reduced by using such in-phase components.

That is, after removal of an external magnetic noise component for the magnetic sensor 1 of interest, the local average value of the magnetic sensor 1 of interest and the adjacent magnetic sensor 1 is taken. Then, the local average value is detected as the measured quantity of the magnetic sensor 1 of interest.

By taking such a local average value, the non-correlated components of the adjacent magnetic sensors 1 are canceled out each other, and the non-correlated components can be reduced.

Figure 5:
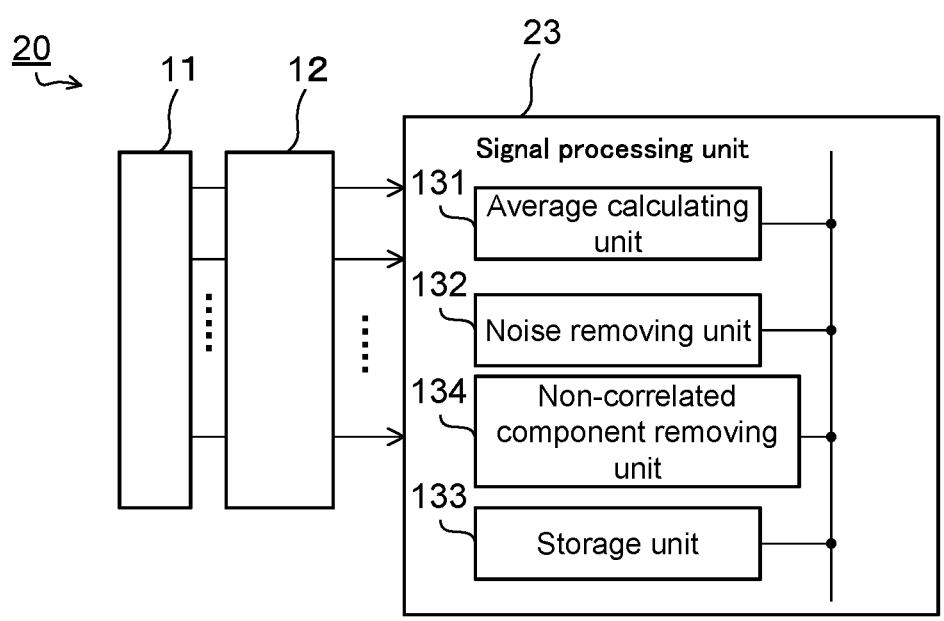
FIG. 5 is a block diagram of the magnetic field measurement apparatus according to a second embodiment.
Figure 6:
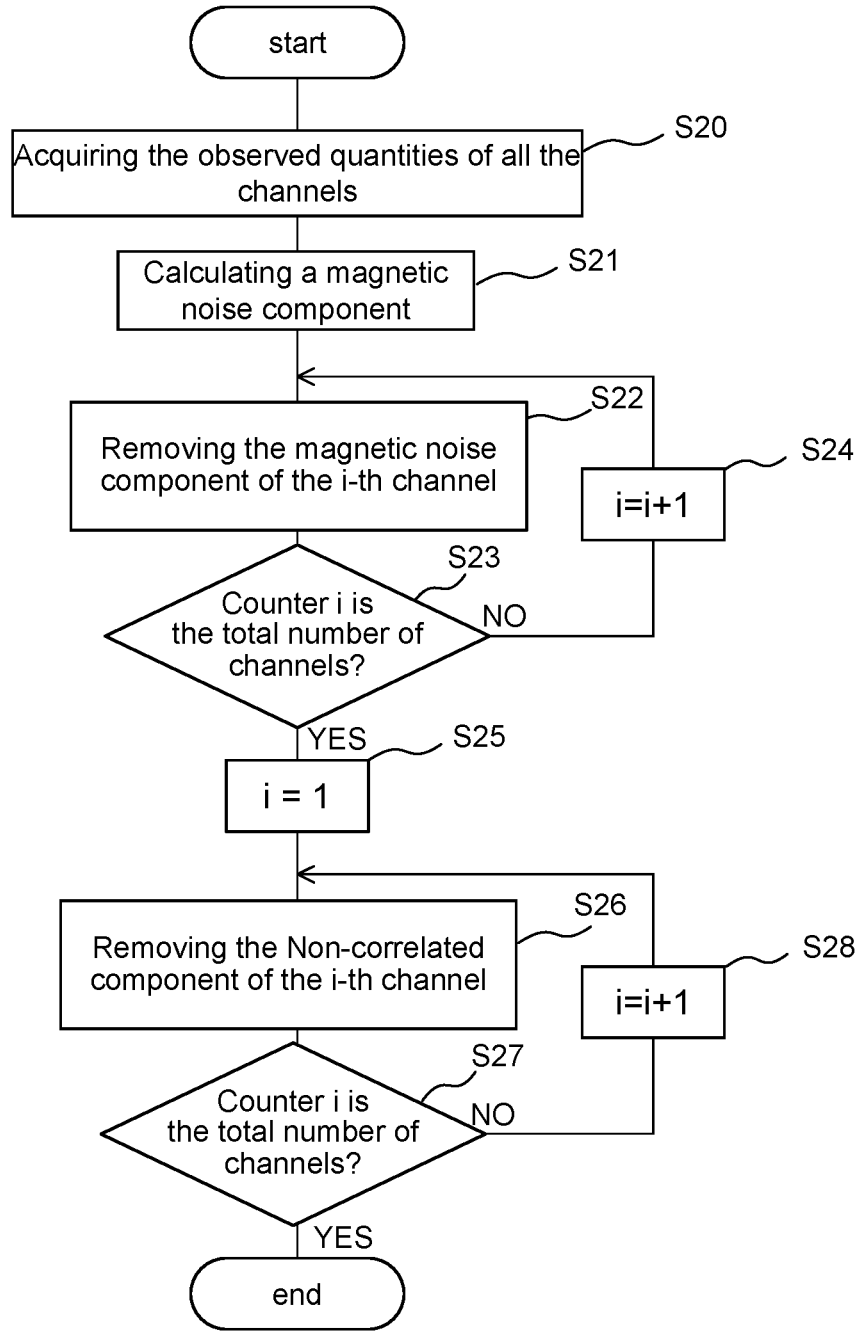
FIG. 6 is a flowchart illustrating the operation of the magnetic field measurement apparatus according to the second embodiment.

FIG. 5 is a block diagram of a magnetic field measurement apparatus 20 according to the present embodiment. FIG. 6 is a flowchart showing an operation of the magnetic field measurement apparatus 20 of FIG. 5.

In the magnetic field measurement apparatus 20 illustrated in FIG. 5, the configuration of the magnetic sensor group 11 and the input circuit 12 is the same as that of the magnetic field measurement apparatus 10 as illustrated in FIG. 1. The magnetic field measurement apparatus 20 is different from the magnetic field measurement apparatus 10 in that a signal processing section 23 further includes a non-correlated component removing circuit 134.

The noise removal operation of the magnetic field measurement apparatus 20 will be described below with reference to FIG. 6.

In FIG. 6, the operation from step S20 to step S24 is the same as the operation in steps S10 to S14 in FIG. 4, so the description thereof will be omitted.

In the present embodiment, non-correlated components are removed in steps S25 to S28.

In step S25, the signal processing unit 13 sets the counter i to the initial value 1.

Next, in step S26, the non-correlated component removing circuit 134 of the signal processing unit 13 removes the non-correlated component from the measured quantity of the magnetic sensor 1 of the i-th channel.

Here, the non-correlated component removing circuit 134 calculates a local average value of the measured quantities of the magnetic sensor 1 of the i-th channel and the magnetic sensor 1 adjacent to the magnetic sensor 1 of the i-th channel. Then, the non-correlated component removing circuit 134 outputs the local average value as the measured quantity after removing the non-correlated component of the magnetic sensor 1 of i-th channel.

Figure 7:
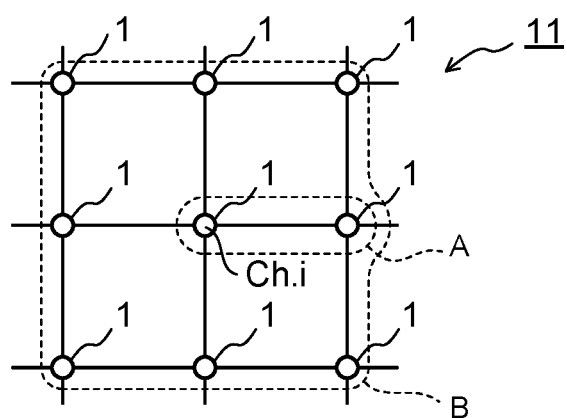
FIG. 7 is a diagram illustrating an example of how to select adjacent channels when removing non-correlated components.

FIG. 7 is a diagram illustrating examples of how to select an adjacent magnetic sensor(s) 1 for removal of the non-correlated component. Note that, FIG. 7 illustrates some of the magnetic sensors 1 included in the magnetic sensor group 11.

In FIG. 7, Ch. i represents the magnetic sensor 1 of the i-th channel of interest. One example of how to select an adjacent magnetic sensor(s) 1 is indicated by a dashed line A. In this case, an average of the measured quantities of two magnetic sensors 1, that is, the magnetic sensor 1 of the i-th channel and one magnetic sensor 1 adjacent in the row or column direction is taken.

According to this way of selecting, the randomly generated non-correlated component decreases to $1/\sqrt{2}$.

As another example is a selection way indicated by a dashed line B. In this case, an average of the total nine measured quantities of the magnetic sensor 1 of the i-th channel and the eight magnetic sensors 1 adjacent in the row, column, and oblique directions is taken.

According to this selection method, the randomly generated non-correlated component decreases to $1/\sqrt{9}$.

The selection way of adjacent channels is not limited to the above example. Generally speaking, when an average value of n measured values is taken, the non-correlated component decreases to $1/\sqrt{n}$ times.

Thereafter, the process proceeds to step S27 in FIG. 6, and the signal processing unit 13 determines whether the removal of the non-correlated component has been completed for the magnetic sensors 1 of all the channels.

When the signal processing unit 13 determines in step S27 that the removal of the non-correlated component has not been completed for the magnetic sensors 1 of all the channels, the process proceeds to step S28, the counter i is incremented by 1 and the process returns to step S26.

On the other hand, when the signal processing unit 13 determines in step S27 that the removal of the non-correlated component has been completed for the magnetic sensor 1 of all the channels, the process is terminated.

As described above, according to the present embodiment, it is possible to reduce non-correlated components that cannot be removed in the first embodiment, by taking the local average of the measured quantities of the magnetic sensors 1.

Third Embodiment

The first and second embodiments are based on the premise that the magnetic noise $N_i$ is applied to all the magnetic sensors 1 with equal values.

However, the magnetic flux of the geomagnetism is concentrated in the vicinity of a magnetic body such as a reinforcing bar in a building, for example. When the sensors are located close to such a place, the magnetic noise component is not applied uniformly to all the sensors, and therefore the noise may not be sufficiently removed.

In the present embodiment, a method of measuring a magnetic field in the case where the intensity of the magnetic noise $N_i$ is distributed with a certain inclination among the positions of the sensors will be described.

Figure 8:
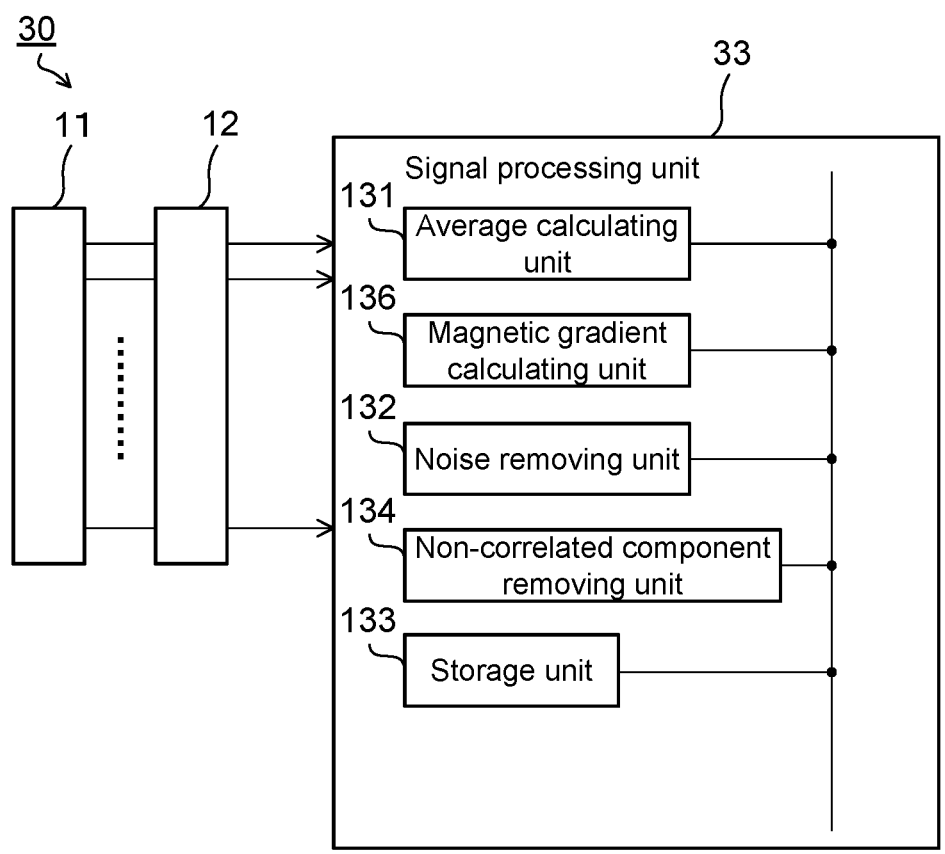
FIG. 8 is a block diagram of a magnetic field measurement apparatus according to a third embodiment.
Figure 10:
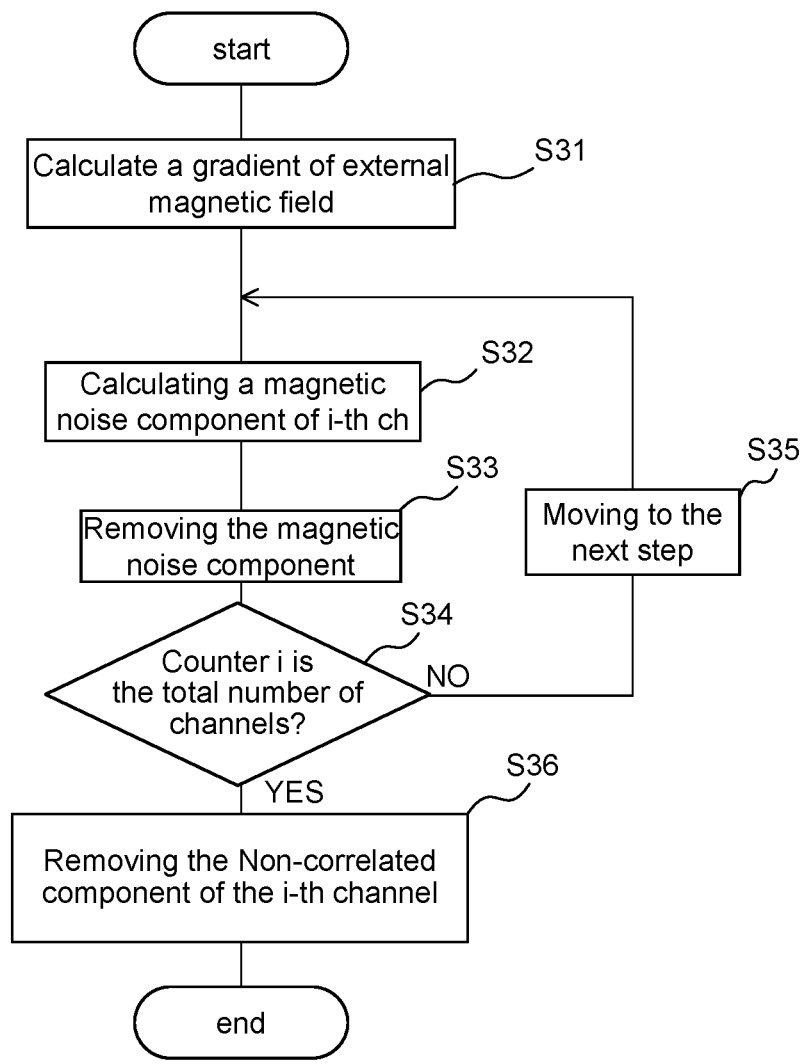
FIG. 10 is a flowchart illustrating the operation of the magnetic field measurement apparatus of FIG. 8.

FIG. 8 is a block diagram of a magnetic field measurement apparatus 30 according to this embodiment. FIG. 10 is a flowchart of the operation of the magnetic field measurement apparatus 30 of FIG. 8.

As illustrated in FIG. 8, the magnetic field measurement apparatus 30 is different from the magnetic field measurement apparatus 20 (see FIG. 5) of the second embodiment in that the magnetic field measurement apparatus 30 includes a magnetic gradient calculating unit 136 in a signal processing unit 33. Other configurations are the same as those of the magnetic field measurement apparatus 20, and the description thereof will be omitted with the same reference numerals given thereto.

In step S31 of FIG. 10, the magnetic gradient calculating unit 136 calculates the magnetic gradient by using the observed quantities of the magnetic sensors 1 located near the peripheral of the magnetic sensor group 11.

Figure 9:
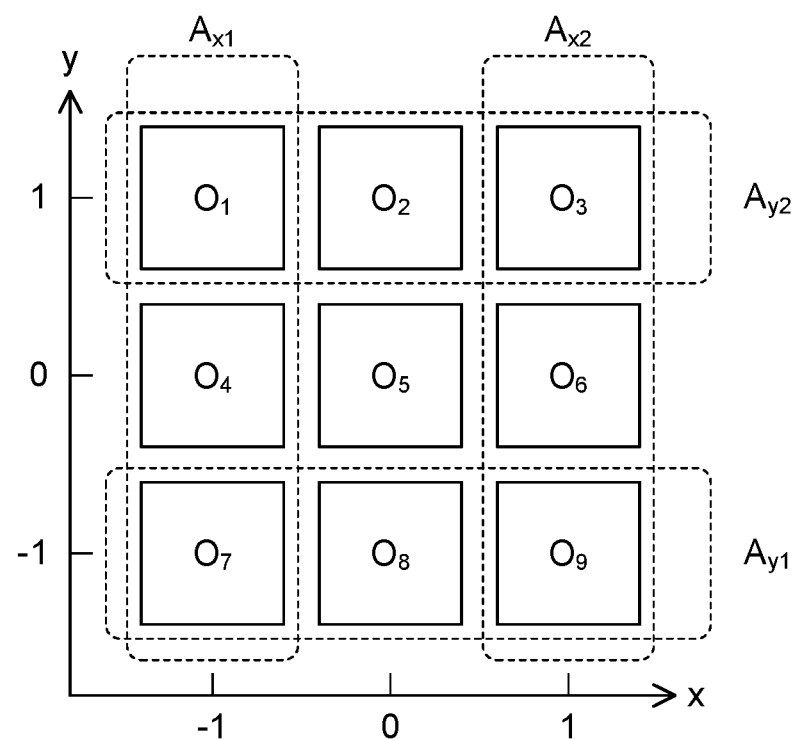
FIG. 9 is a diagram illustrating a method of obtaining a magnetic field gradient in the third embodiment.

FIG. 9 is a diagram illustrating a method of obtaining the gradient of an external magnetic field.

The example of FIG. 9 is described on the assumption that the magnetic sensor group 11 is composed of nine magnetic sensors 1 in 3 rows×3 columns for convenience of description.

In the magnetic sensor group 11 of this example, the magnetic sensors 1 of the respective channels are arranged at positions −1, 0, 1 in the x axis direction and at positions −1, 0, 1 in the y axis direction. Thus, the relative positional relationship among the magnetic sensors 1 in the magnetic sensor group 11 is predetermined.

The magnetic gradient calculating unit 136 calculates the magnetic gradient by using the position coordinates of the magnetic sensors 1.

First, a method of calculating the magnetic gradient in the x direction is described.

The magnetic gradient calculating unit 136 extracts the observed quantities $O_1$, $O_4$, and $O_7$ of the three magnetic sensors 1 whose x coordinate is −1 in the magnetic sensor group 11, and takes an average $A_{x1}$ of them.

$$A_{x1} = \frac{O_1 + O_4 + O_7}{3} \quad (3\text{-}1)$$

Next, the magnetic gradient calculating unit 136 extracts the observed quantities $O_3$, $O_6$, and $O_9$ of the three magnetic sensors 1 whose x coordinate is 1, and takes an average $A_{x2}$ of them.

$$A_{x2} = \frac{O_3 + O_6 + O_9}{3} \quad (3\text{-}2)$$

Thereafter, the magnetic gradient calculating unit 136 calculates the gradient in the x-axis direction based on the averages $A_{x1}$ and $A_{x2}$ in accordance with the following expression.

$$g_x = \frac{A_{x2} - A_{x1}}{2} \quad (3\text{-}3)$$

Next, a method of calculating the magnetic gradient in the y-axis direction is described.

The magnetic gradient calculating unit 136 extracts the observed quantities $O_7$, $O_8$, and $O_9$ of the three magnetic sensors 1 whose y coordinate is −1 in the magnetic sensor group 11, and takes an average $A_{y1}$ of them.

$$A_{y1} = \frac{O_7 + O_8 + O_9}{3} \quad (3\text{-}4)$$

The magnetic gradient calculating unit 136 extracts the observed quantities $O_1$, $O_2$, and $O_3$ of the three magnetic sensors 1 having the y coordinate of 1, and takes an average $A_{y2}$ of them.

$$A_{y2} = \frac{O_1 + O_2 + O_3}{3} \quad (3\text{-}5)$$

Then, the magnetic gradient calculating unit 136 calculates the gradient in the y-axis direction based on the averages $A_{y1}$ and $A_{y2}$ in accordance with the following expression.

$$g_y = \frac{A_{y2} - A_{y1}}{2} \quad (3\text{-}6)$$

Thus, the gradient of the magnetic noise component is obtained.

Next, in step S32, the magnetic gradient calculating unit 136 calculates the magnetic noise $N_i$ of the magnetic sensor 1 of the first channel i.

Here, $N_i$ is expressed by the following equation.

$$N_i = (g_x x_i + g_y y_i) \cdot f \quad (3\text{-}7)$$

Note that f is an average of observed quantities of all the channels, and the average value calculating unit 131 calculates the average f.

The position $(x_i, y_i)$ of the i-th magnetic sensor 1 is known as predetermined values. Therefore, the magnetic gradient calculating unit 136 calculates the magnetic noise $N_i$ of the i-th magnetic sensor 1 in accordance with the formula (3-7).

Next, in step S33, the noise removing unit 132 calculates the measured quantity $S_i$ by using the magnetic noise $N_i$.

Here, for the i-th magnetic sensor 1, the measured quantity $S_i$ is expressed by the following expression as subtracting the magnetic noise $N_i$ from the observed quantity $O_1$.

$$S_i = O_i - N_i \tag{3-8}$$

That is, the noise removing unit 132 subtracts the magnetic noise $N_i$, obtained based on the expression (3-7), from the observed quantity $O_i$ of the i-th magnetic sensor 1 based on the expression (3-8). Thereby the noise is removed and the measured quantity $S_i$ of the magnetic sensor 1 is obtained.

Thereafter, the process proceeds to step S34, where the signal processing unit 33 determines whether or not noise removal has been completed for all the channels. If the noise removal has not been completed for all the channels, the signal processing unit 33 counts up the counter to move the next channel (Step S35), and iterates the processing of steps S32 and S33.

On the other hand, if the signal processing unit 33 determines in step S34 that the noise removal has been completed for all the channels, the process proceeds to step S36. Then, the non-correlated component removing circuit 134 removes the non-correlated components.

The removal of the non-correlated components may be performed in the same manner as described in steps S25 to S28 in FIG. 6.

According to the present embodiment, magnetic noise can be removed as described above even if the distribution of the intensity of the magnetic noise $N_i$ from the external magnetic field is inclined.

Fourth Embodiment

In the above-described embodiment, the correction such as noise removal is performed on the assumption that all the magnetic sensors 1 have completely equal output properties. However, the actual magnetic sensor 1 has unique output properties. Even if the same magnetic field is applied, the value of the output voltage may vary among the magnetic sensors 1. It is also necessary to consider the influence of variations in the output properties among the amplifier circuits 121.

The influence of the output properties of the magnetic sensor 1 and the amplifier circuit 121 appears as a component unique to each channel. Therefore, such unique component cannot be removed by the foregoing method of subtracting the component common to the observed quantities in all the channels in the first embodiment.

One conceivable way to remove the influence of variations in the output property among the magnetic sensors 1 is to adjust the output properties, themselves, by using variable resistors attached to the respective magnetic sensors 1. However, such adjustment is very time consuming, and in addition is not practical if the number of the magnetic sensors 1 increases.

Therefore, in the present embodiment, description will be provided for a magnetic field measurement method capable of removing the influence of variations in the output property among the magnetic sensors 1 of all the channels.

Figure 11:
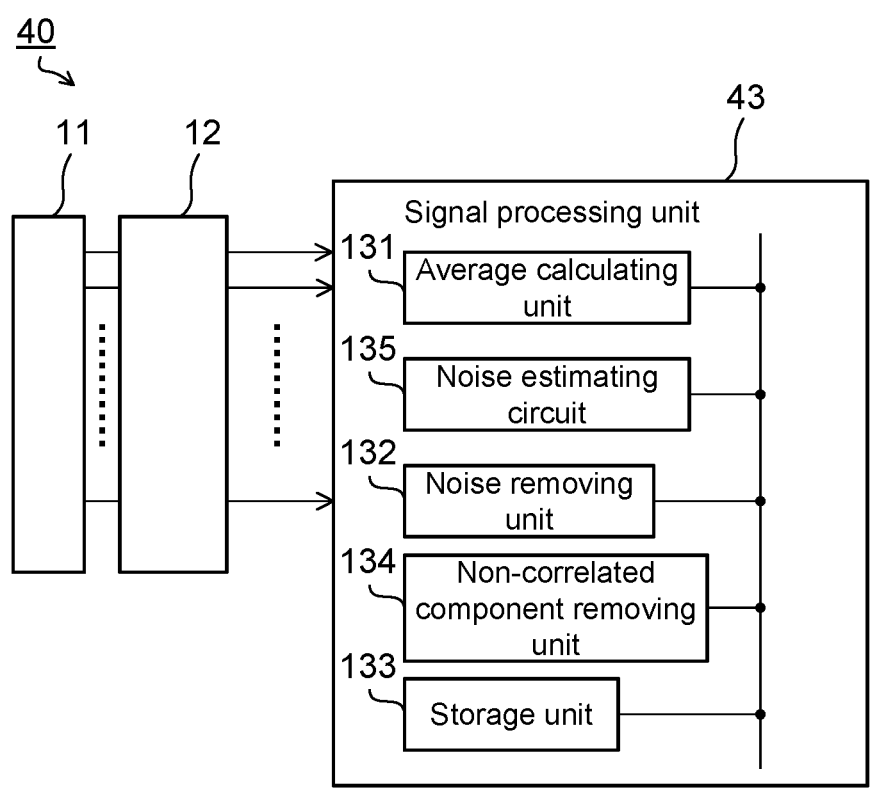
FIG. 11 is a block diagram of a magnetic field measurement apparatus according to a fourth embodiment.

FIG. 11 is a block diagram of a magnetic field measurement apparatus 40 according to the present embodiment. In the magnetic field measurement apparatus 40 of the present embodiment, the same reference numerals are given to the same components as those of the magnetic field measurement apparatuses 10 to 30 of FIG. 1, and a detailed description thereof will be omitted.

As illustrated in the FIG. 11, the magnetic field measurement apparatus 40 is different from the magnetic field measurement apparatus 20 (see FIG. 5) in a signal processing unit 43.

The signal processing unit 43 comprises a noise estimating circuit 135 in addition to the average value calculating unit 131, the noise removing unit 132, the storage unit 133, and the non-correlated component removing circuit 134. The noise estimating circuit 135 calculates noise considering the influence of the output property of each channel.

Hereinafter, the principle of the noise removal method in the present embodiment will be described.

As shown in FIG. 2, the magnetic sensor group 11 includes a plurality of magnetic sensors 1. Here, noise removal of the magnetic sensor 1 of an i-th channel selected from them will be described.

First, consider a detection signal (observed quantity) at a time t of the magnetic sensor 1 of the i-th channel.

Here, the magnetic field component from the living body as the object is denoted by $S_i(t)$ and the magnetic noise at the position of the magnetic sensor 1 of i-th channel is denoted by $N_i(t)$.

Letting the observed quantity obtained from the i-th magnetic sensor 1 be $O_i(t)$, the magnetic field component $S_i(t)$ from the object is expressed as follows.

$$S_i(t) = O_i(t) - N_i(t) \tag{4-1}$$

Note that, the observed quantity $O_i(t)$ is the measurement data itself of the magnetic sensor 1 of the i-th channel.

According to the equation (1), the magnetic field component $S_i(t)$ from the object to be determined can be found by subtracting the magnetic noise $N_i(t)$ from the actually measured observed quantity $O_i(t)$.

However, the magnetic field component $S_i(t)$ from the object is unknown and the magnetic noise $N_i(t)$ is also unknown. The magnetic field component $S_i(t)$ from the object cannot be obtained directly by the equation (4-1).

Here, the average value of the observed quantities of the magnetic sensors 1 of all the channels reflects the magnetic noise component from the external magnetic field, as described in the first embodiment. Therefore, it is considered that there is a certain correlation between the unknown magnetic noise $N_i(t)$ and the average value of the observed quantities of the magnetic sensors 1 of all the channels. This correlation is considered to be approximated by using an offset component b entering the magnetic sensor 1 of the channel of interest and a component based on an output property (sensitivity) peculiar to the channel.

That is, in the present embodiment, the unknown magnetic noise $N_i(t)$ is considered to be approximated by the following linear expression.

$$N_i(t) = af(t) + b \tag{4-2}$$

Here, the variable a is a component that reflects the sensitivity (output property) of the magnetic sensor 1 of the i-th channel. In this embodiment, the sensitivity of the magnetic sensor 1 means a coefficient indicating the ratio of the change amount of the output signal of the channel including the magnetic sensor 1 and the amplifier circuit 121 to the fluctuation of the magnetic field. The variable b is an offset component applied to the magnetic sensor 1 and the amplifier circuit 121 of the i-th channel.

f(t) represents an average value of the observed quantities $O(t)$ at the time t of the magnetic sensors 1 of all the channels. This average value is obtained by the following expression.

$$f(t) = \frac{1}{n}\sum_{i=1}^{n} O_i(t) \qquad (4\text{-}3)$$

In the above equation (4-3), n represents the total number of channels.

Next, a method of obtaining an unknown magnetic noise $N_i(t)$ will be described.

Figure 12:
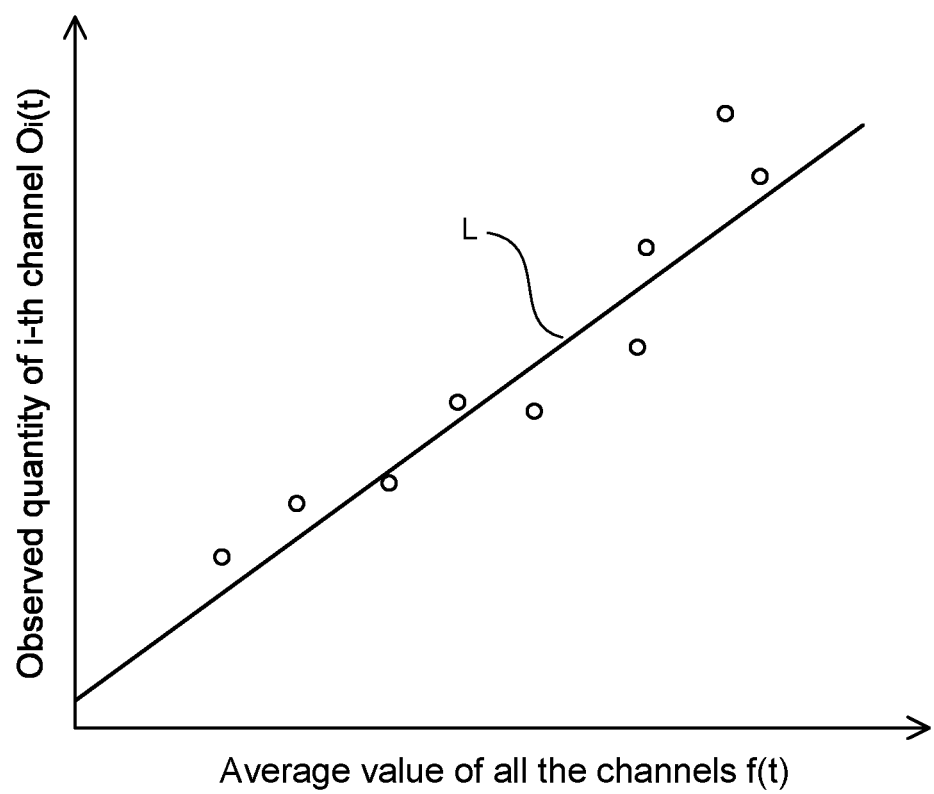
FIG. 12 is a diagram illustrating an example of a correlation between the observed quantity of the magnetic sensor and the average value of the observed quantities of all the channels.

FIG. 12 is a diagram illustrating the correlation between the observed quantity O(t) of the magnetic sensor 1 of the channel of interest and the average value f(t) of the magnetic sensors 1 of all the channels. Note that, the vertical axis represents the observed quantity O(t) and the horizontal axis represents the average value f(t).

The observed quantity O(t) of the magnetic sensor 1 of interest includes S(t) which is a magnetic field component (measured quantity) from the object and an external magnetic noise component $N_i(t)$.

Of them, the magnetic field component from the object is several tens of pico-Tesla for example, whereas the magnetic noise component is as large as several milli-Tesla, so the magnetic noise component $N_i(t)$ occupies most of the observed quantity O(t).

Therefore, if an approximate straight line between the observed quantity O(t) and the average value f(t) in FIG. 12 is found, the variables "a" and "b" in the equation (4-2) representing the correlation between the magnetic noise component $N_i(t)$ and the average value f(t) are determined.

That is, the sensitivity coefficient unique to the magnetic sensor 1, the variable "a" of the equation (4-2), is determined as the slope of the approximate straight line L in FIG. 12, and the offset of the magnetic sensor 1, the variable "b" of the equation (4-2), is determined as the intercept of the approximate straight line L.

The external magnetic field varies from moment to moment due to the movement of the object or the noise from the AC power source. Accordingly, the observed quantities O(t) of the magnetic sensors 1 and the average value f(t) thereof change every moment by moment.

Therefore, if a sufficient amount of the combinations of the observed quantity O(t) and the average value f(t) can be obtained by repeating the operation of obtaining the observed quantities O(t) and the average value f(t) at predetermined sampling intervals, then, the correlation between the magnetic noise $N_i(t)$ and the average value f(t) can be obtained with high accuracy.

As a result, the magnetic noise component $N_i(t)$ incorporating the output property of each of the magnetic sensors 1 can be obtained.

In order to acquire the above measurement data, the magnetic field measurement apparatus 40 repeats the measurement by the magnetic sensors 1 of all the channels included in the magnetic sensor group 11 at fixed sampling intervals. The data of the measurement results are stored in the storage unit 133 of the signal processing unit 43. For example, the signal processing unit 43 acquires m−1th to 0th observed quantities $O_i(t)$ for m current and past samplings where t=0 means the current time.

For example, if the object is a heart, the sampling frequency may be twice or more times the frequency of the nerve signal transmitted to the cardiac muscles, and the sampling interval may be set to, for example, 5 milliseconds or less.

The signal processing unit 43 calculates the variables a and b for determining the magnetic noise component $N_i(t)$ by using the m observed quantities $O_i(t)$ and the average value f(t).

First, the sum of squares j of the difference between the magnetic noise $N_i(t)$ and the observed quantity $O_i(t)$ is obtained by the following equation.

$$j = \sum_{t}^{m} \{O_i(t) - (af(t) + b)\}^2 \qquad (4\text{-}4)$$

Here, "m" is the number of samplings, represents a section in the time axis direction, to which the least squares method is applied.

Next, the coefficient a and the intercept b of the straight line (af(t)+b) under the condition that j gives the minimum value are obtained based on the following equation.

$$\frac{\partial j}{\partial a} = \frac{\partial j}{\partial b} = 0 \qquad (4\text{-}5)$$

The above equation is calculated as follows.

$$\frac{\partial j}{\partial a} = \qquad (4\text{-}6)$$

$$\frac{\partial}{\partial a}\sum_{t}^{m}\{O_i(t)^2 - 2aO_i(t)f(t) - 2bO_i(t) + a^2f(t)^2 + 2abf(t) + b^2\} =$$

$$\sum_{t}^{m}\{-2O_i(t)f(t) + 2af(t)^2 + 2bf(t)\} = 0$$

$$\frac{\partial j}{\partial b} = \sum_{t}^{m}\{-2O_i(t) + 2af(t) + 2b\} = 0 \qquad (4\text{-}7)$$

These simultaneous equations are transformed into the following equation (4-8).

$$\begin{pmatrix} \sum_{t}^{m} f(t)^2 & \sum_{t}^{m} f(t) \\ \sum_{t}^{m} f(t) & m \end{pmatrix} \begin{pmatrix} a \\ b \end{pmatrix} = \begin{pmatrix} \sum_{t}^{m} O_i(t)f(t) \\ \sum_{t}^{m} O_i(t) \end{pmatrix} \qquad (4\text{-}8)$$

Further, the equation is transformed as follows.

$$A = \begin{pmatrix} \sum_{t}^{m} f(t)^2 & \sum_{t}^{m} f(t) \\ \sum_{t}^{m} f(t) & m \end{pmatrix} \qquad (4\text{-}9)$$

$$B = \begin{pmatrix} \sum_{t}^{m} O_i(t)f(t) \\ \sum_{t}^{m} O_i(t) \end{pmatrix} \qquad (4\text{-}10)$$

$$x = \begin{pmatrix} a \\ b \end{pmatrix} \qquad (4\text{-}11)$$

As described above, a determinant of Ax=B is obtained. Therefore, the variables "a" and "b" are obtained by calculating x=A−1 B. That is, by multiplying the inverse matrix A−1 and the matrix B, the variables "a" and "b" can be obtained by the following equations.

$$a = \frac{m\sum_t^m O_i(t)f(t) - \sum_t^m O_i(t)\sum_t^m f(t)}{m\sum_t^m f(t)^2 - \left\{\sum_t^m f(t)\right\}^2} \quad (4\text{-}12)$$

$$b = \frac{\sum_t^m O_i(t)\sum_t^m f(t)^2 - \sum_t^m O_i(t)f(t)\sum_t^m f(t)}{m\sum_t^m f(t)^2 - \left\{\sum_t^m f(t)\right\}^2} \quad (4\text{-}13)$$

The corrected magnetic noise component is obtained by performing the calculation of the above-mentioned equations (4-12) and (4-13). That is, the signal processing unit 43 reads the observed quantities O(t) of the magnetic sensors 1 of all the channels in the time range from the time 0 to the time m−1, and calculates the average value f(t). Then, the signal processing unit 43 substitutes the observed quantity $O_i(t)$ of the magnetic sensor 1 of the i-th channel of interest into the equations (4-12) and (4-13) to find the variables "a" and "b".

By this calculation, the approximate straight line 91 as shown in FIG. 12 is obtained, and then the magnetic noise component $N_i(t)$ at the current sampling time point t is obtained by substituting the found values of the variables a and b to af(t)+b.

In the above calculation, the magnetic noise $N_i(t)$ is obtained under the condition that the sum of squares j of the difference between the magnetic noise $N_i(t)$ and the observed quantity $O_i(t)$ is to be minimized.

This is because, in the observed quantity $O_i(t)$, the magnetic field component $S_i(t)$ from the object is several tens of pico-Tesla, whereas the external magnetic noise component $N_i(t)$ is several milli-Tesla, which is overwhelmingly larger than that of the magnetic field component from the object, and occupies the majority of the observed quantity $O_i(t)$. In addition, the magnetic field component $S_i(t)$ from the object is detected as an alternating current component such as a component from, for example, heart beats. If samplings are conducted for a sufficiently long time, the average value of the magnetic field component $S_i(t)$ from the object approaches substantially to zero.

For the above reasons, if the number of samplings is sufficiently large, an approximate function of the average value f (t) can be obtained under the condition that gives the minimum value of the sum of squares j of the difference between the magnetic noise component $N_i(t)$ and the observed quantity $O_i(t)$.

In this manner, the output (sensitivity) output property peculiar to the magnetic sensor 1 of each channel is taken into account in the correction calculation, and no adjustment work is required for each of the magnetic sensors 1.

Next, calculation of the magnetic signal $S_i(t)$ from the object will be described.

The magnetic noise component $N_i(t)$ at the current sampling time t is obtained by substituting the values of the variables a and b, which area derived by calculating the equations (4-12) and (4-13), and the average value f(t) at the current sampling time t into the equation (4-2).

Next, the magnetic signal $S_i(t)$ from the object is calculated by subtracting the value of the magnetic noise component $N_i(t)$ from the observed quantity $O_i(t)$, as in following equation.

$$S_i(t)=O_i(t)-(af(t)+b) \quad (4\text{-}14)$$

Thus, the magnetic signal $S_i(t)$ of the magnetic sensor 1 of the i-th channel at the current sampling time t can be obtained.

The values of the variables "a" and "b" are different among the channels of the magnetic sensors 1. The signal processing unit 43 calculates the equations (4-1) to (4-14) for the magnetic sensor 1 of every channel in order to obtain the measured quantities $S_i(t)$ from all the magnetic sensors 1 of the other channels. In this way, it is possible to detect a weak magnetic signal produced by the object by using all the magnetic sensors 1 included in the magnetic sensor group 11.

Figure 13:
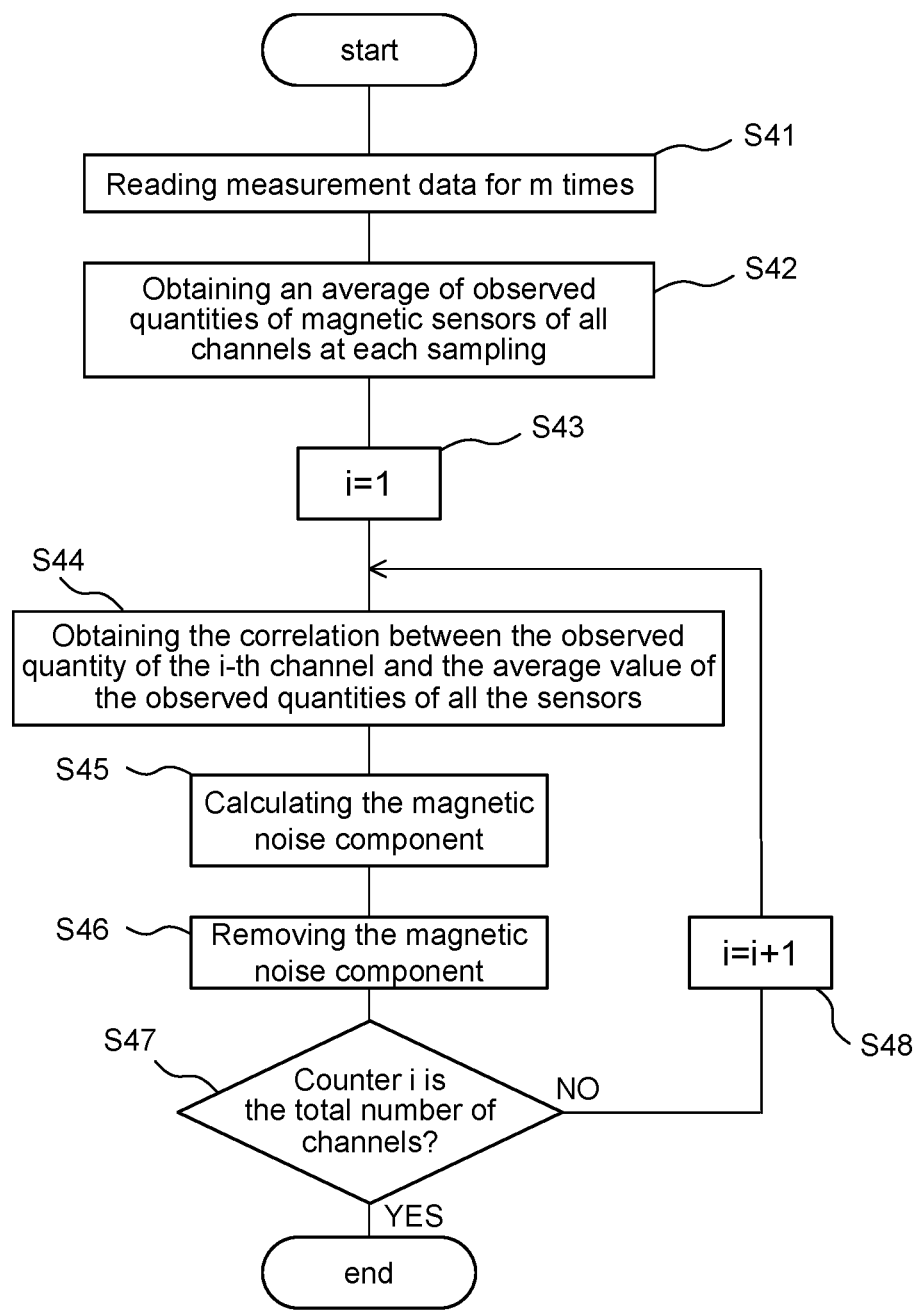
FIG. 13 is a flowchart illustrating the operation of the magnetic field measurement apparatus of FIG. 11.

The operation of the magnetic field measurement apparatus 40 will be described based on the above magnetic field measurement method. Here, FIG. 13 is a flowchart showing the operation of the magnetic field measurement apparatus 40 of the present embodiment.

First, in step S41, the magnetic field measurement apparatus 40 acquires the observed quantities from the magnetic sensors 1 of all the channels at a certain sampling time and stores them in the storage unit 133.

The magnetic field measurement apparatus 40 repeats the measurement of the magnetic field at fixed sampling intervals, thereby acquiring the measurement data (observed quantities) of the magnetic sensors 1 of all channels for the m current and past samplings. The acquired measurement data is stored in the storage unit 133.

Next, in step S 42, the average value calculating unit 131 calculates the average value of the observed quantities of all the channels at each sampling time.

Next, the process proceeds to step S43, and the value of the counter i is set to the initial value "1".

In step S44, the noise estimating circuit 135 finds the correlation between the observed quantity of the i-th channel and the average value calculated in step S42.

That is, the noise estimating circuit 135 substitutes the average value obtained in step S 42 and the value of the observed quantity of the i-th channel into the equations (4-12) and (4-13), so that the values of the variables a and b are obtained.

Next, in step S45, the noise estimating circuit 135 calculates the value of the corrected magnetic noise component at the time t. That is, the noise estimating circuit 135 calculates the magnetic noise component $N_i(t)$ by the expression af(t)+b using the values of the variables a and b obtained in step S44 and the average value of the observed quantities at the time t.

Next, in step S46, the noise removing unit 132 removes noise from the observed quantity of the magnetic sensor 1 of the i-th channel. That is, the noise removing unit 132 subtracts the magnetic noise component $N_i(t)$ obtained in step S45 from the observed quantity $O_i(t)$ of the i-th channel at the time t.

Next, in step S47, the signal processing unit 13 determines whether noise removal has been completed for all the channels.

If it is determined in step S47 that noise removal has not been completed for all the channels, the process proceeds to step S48 where the counter i is incremented by 1, and then the processing in steps S44 to S46 is repeated.

On the other hand, if it is determined in step S47 that noise removal has been completed for all the channels, the process is terminated.

By repeating the above operation by the magnetic field measurement apparatus 40, the noise removal of all the magnetic sensors 1 is completed.

If necessary, after the processing of step S41 to step S48, the non-correlated component may be removed by the method described in the second embodiment.

As described above, the output from each magnetic sensor 1 included in the magnetic sensor group 11 reflects the output (sensitivity) output property peculiar to the magnetic sensor and the unknown offset component due to the external magnetic field.

Conventionally, in order to perform accurate measurement, it has been necessary to measure and adjust the sensitivity output property of each magnetic sensor 1 under the condition that the external magnetic field is minimized, and such complicated work has been required.

In contrast to this, according to the present embodiment, it is possible to remove the influence of the variation of the output property of the magnetic sensor 1 together with the external magnetic field noise component, and thus to measure the weak magnetic field without performing any complicated adjustment work.

Modification of Fourth Embodiment

Figure 14:
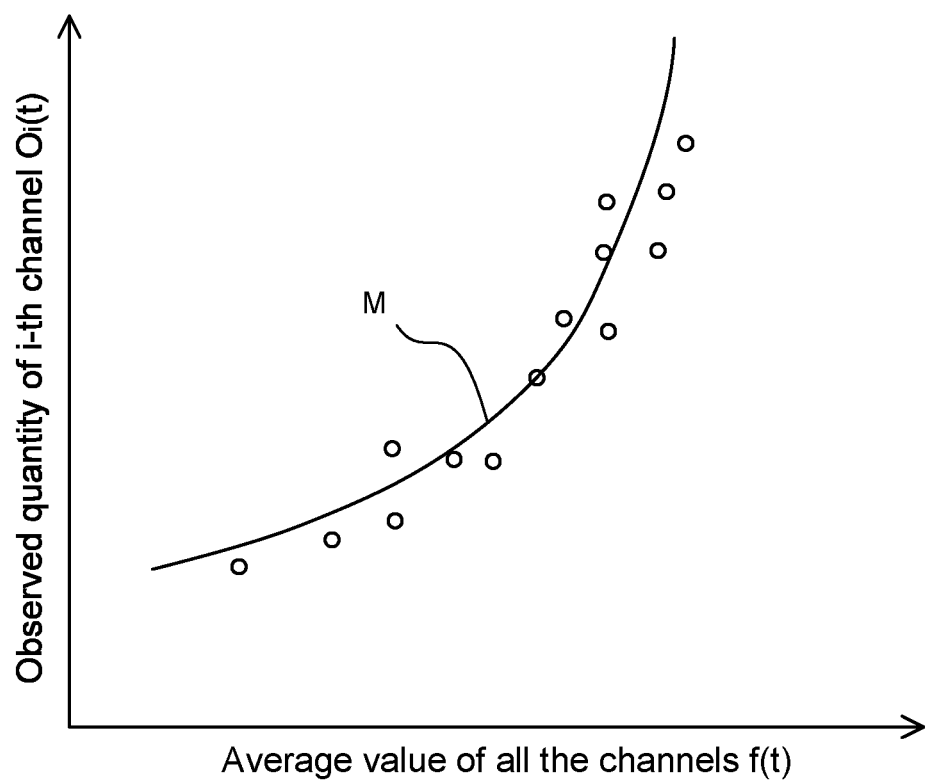
FIG. 14 is a diagram illustrating another example of the correlation between the observed quantity of the magnetic sensor and the average value of the observed quantities of all the channels.

FIG. 14 is a diagram illustrating a method of removing a magnetic noise component according to a modification of the fourth embodiment.

As illustrated in FIG. 14, an approximation based on a high-order polynomial curve M may be used to express a correlation between the average value f(t) of all channels and the observed quantity $O_i(t)$ of the magnetic sensor 1 of interest. Thereby the accuracy of approximation can be improved.

In the present modification, a polynomial curve M is found as an approximate curve between the average value f(t) of all the channels and the observed quantity $O_i(t)$ of the magnetic sensor 1 of interest.

In the following, an example where an approximation uses a quadratic polynomial is described. The magnetic noise $N_i(t)$ is approximated by the following equation.

$$N_i(t) = c_1 f^2(t) + c_2 f(t) + c_3 \quad (4\text{-}15)$$

First, the sum of squares j of the difference between the magnetic noise $N_i(t)$ and the observed quantity $O_i(t)$ is obtained. Then, the variables $c_2$, and $c_3$ of the expression $(c_1 f^2(t) + c_2 f(t) + c_3)$ of a curve that minimizes the sum of squares j are obtained by the least squares method. Thereby, an approximate curve of this variation is obtained.

In order to increase the number of samplings, the measurement frequency may be increased. As a result, a more accurate approximate value of the magnetic noise component $N_i$ can be obtained.

As described above, according to the present modification, the magnetic field noise $N_i$ can be obtained more accurately, and the measurement accuracy of the measured quantity $S_i$ buried in the noise can be further enhanced.

Fifth Embodiment

Figure 15:
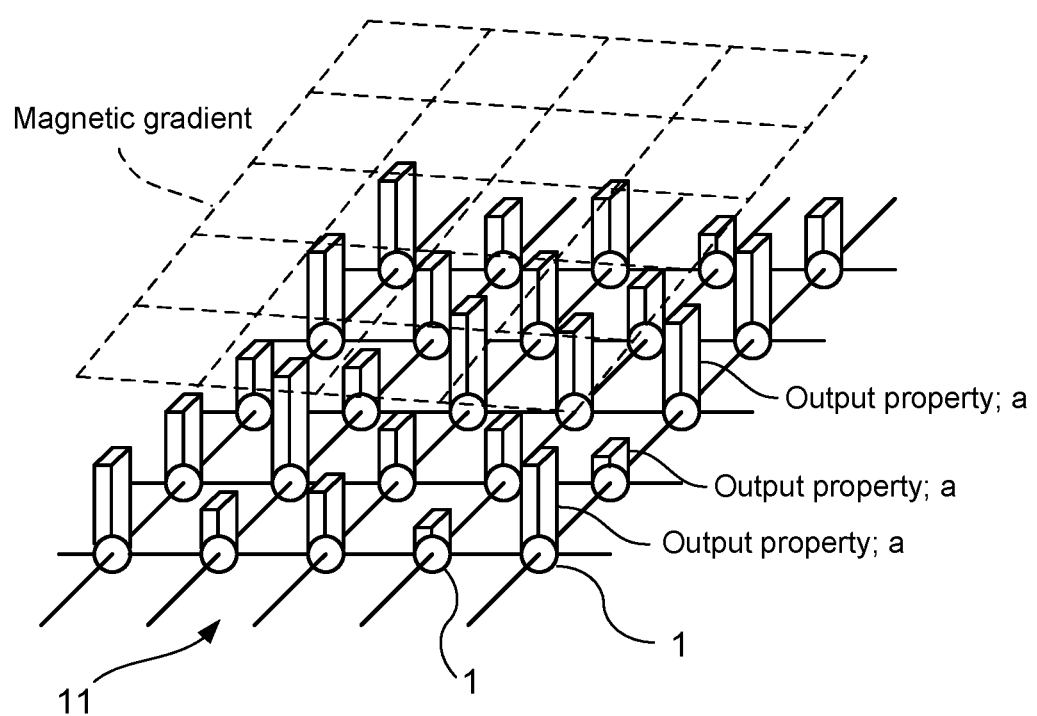
FIG. 15 is a diagram schematically illustrating noise components to be removed in a fifth embodiment.

FIG. 15 is a schematic diagram of noise components to be removed in the present embodiment.

In the FIG. 15, a magnetic sensor group 11 includes magnetic sensors 1 of 5 rows×5 columns. A bar extending upward from the magnetic sensor 1 schematically illustrates output properties (gain properties) of the magnetic sensors 1 and the amplifier circuits 121.

As shown in the figure, a magnetic gradient may occur depending on an environment in which the magnetic sensor group 11 is actually used. Even in such an environment, correction of variations in the output property among the magnetic sensors 1 and the amplifier circuits 121 is required.

In the present embodiment, a method of simultaneously removing the variations in the output property among the magnetic sensors 1 and the noise components due to the magnetic gradient will be described.

Figure 16:
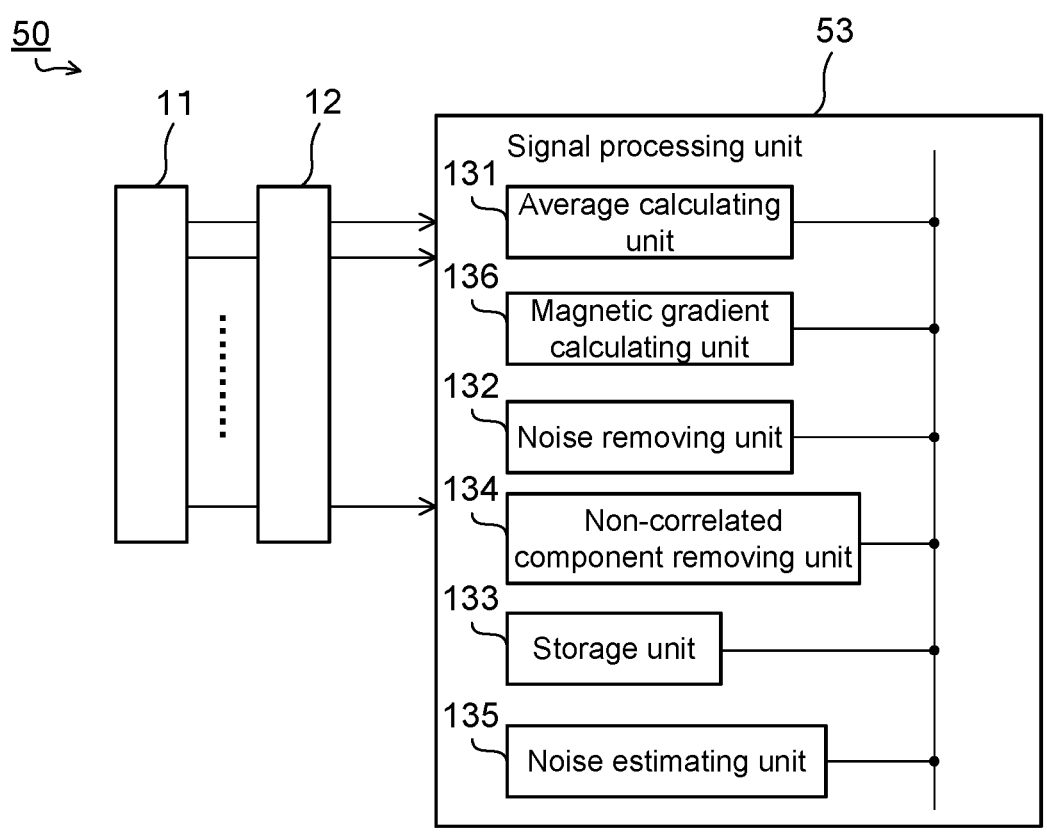
FIG. 16 is a block diagram of a magnetic field measurement apparatus according to the fifth embodiment.

FIG. 16 is a block diagram of a magnetic field measurement apparatus 50 according to the present embodiment.

As illustrated in FIG. 16, the magnetic field measurement apparatus 50 of the present embodiment is different from the magnetic field measurement apparatus 40 (see FIG. 11) of the fourth embodiment in that the apparatus 50 has a magnetic gradient calculating unit 136 in a signal processing unit 53. Other configurations are the same as those of the magnetic field measurement apparatus 40, and description thereof is omitted with the same components denoted by the same reference numbers.

Hereinafter, a method of removing noise components in the present embodiment will be described together with the operation of the magnetic field measurement apparatus 50.

First, the average value calculating unit 131 of the magnetic field measurement apparatus 50 calculates an average value f(t) of observed quantities of the magnetic sensors 1 of all the channels. The average value f(t) is obtained by the following expression.

$$f(t) = \frac{1}{n} \sum_i^n O_i(t) \quad (5\text{-}1)$$

Here, "n" is the total number of channels, and $O_i(t)$ is the observed quantity of the i-th channel.

Next, the magnetic gradient calculating unit 136 calculates the magnetic gradient by using the position coordinates of the magnetic sensors 1 based on the observed quantities of all the channels.

Figure 17:
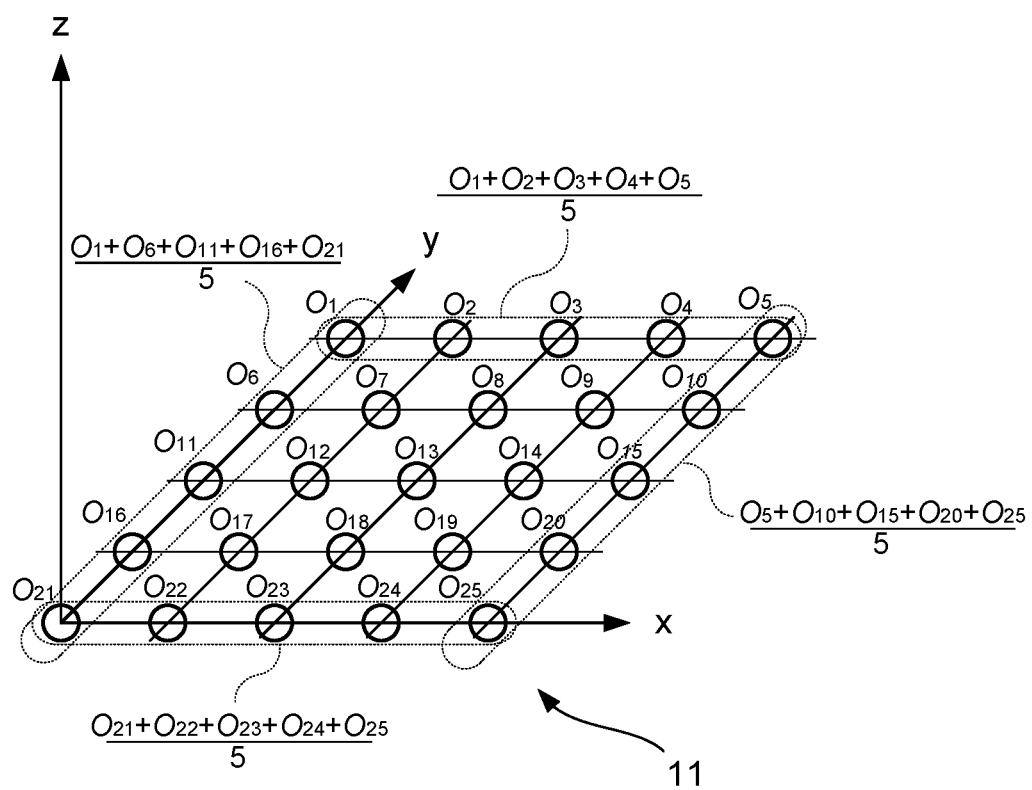
FIG. 17 is a diagram illustrating a method of calculating a magnetic gradient in the fifth embodiment.

FIG. 17 is a view illustrating a method of calculating a magnetic gradient in the present embodiment. Here, a magnetic sensor group 11 consisting of 25 magnetic sensors 1 of 5 rows×5 columns will be described as an example.

First, a method of calculating the magnetic gradient in the x direction will be described.

The magnetic gradient calculating unit 136 extracts the observed quantities $O_1$, $O_6$, $O_{11}$, $O_{16}$, $O_{21}$ of the five magnetic sensors 1 having the smallest x coordinate in the magnetic sensor group 11, and calculates the average value $A_{x1}$ of them.

$$A_{x1} = \frac{O_1 + O_6 + O_{11} + O_{16} + O_{21}}{5} \quad (5\text{-}2)$$

Next, the magnetic gradient calculating unit 136 extracts the observed quantities $O_5$, $O_{10}$, $O_{15}$, $O_{20}$, $O_{25}$ of the five magnetic sensors 1 having the largest x coordinate, and calculates the average value $A_{x2}$ of them.

$$A_{x2} = \frac{O_5 + O_{10} + O_{15} + O_{20} + O_{25}}{5} \quad (5\text{-}3)$$

Thereafter, the magnetic gradient calculating unit 136 calculates the gradient in the x-axis direction based on the following equation using the above-mentioned $A_{x1}$ and $A_{x2}$. It is assumed that the length of the magnetic sensor group 11 in the X direction is 4.

$$g_x = \frac{A_{x2} - A_{x1}}{4} \quad (5\text{-}4)$$

Next, a method of calculating the magnetic gradient in the y-axis direction will be described.

The magnetic gradient calculating unit 136 extracts the observed quantities $O_{21}$, $O_{22}$, $O_{23}$, $O_{24}$, $O_{25}$ of the five magnetic sensors 1 having the smallest y coordinate in the magnetic sensor group 11, and calculates the average value $A_{y1}$ of them.

$$A_{y1} = \frac{O_{21} + O_{22} + O_{23} + O_{24} + O_{25}}{5} \quad (5\text{-}5)$$

Also, the magnetic gradient calculating unit 136 extracts the observation quantities $O_1$, $O_2$, $O_3$, $O_4$, $O_5$ of the five magnetic sensors 1 having the largest y coordinate, and calculates the average value $A_{y2}$ of them.

$$A_{y2} = \frac{O_1 + O_2 + O_3 + O_4 + O_5}{5} \quad (5\text{-}6)$$

Thereafter, the magnetic gradient calculating unit 136 calculates the gradient in the y-axis direction based on the following equation using the above-mentioned $A_{y1}$ and $A_{y2}$.

$$g_y = \frac{A_{y2} - A_{y1}}{4} \quad (5\text{-}7)$$

Thus, the gradient of the magnetic noise component is determined.

Next, the noise estimating circuit 135 calculates an approximate value of a noise and offset component due to external magnetic gradient.

In this embodiment, it is assumed that the observed quantity $O_i(t)$ of the i-th channel is expressed by an approximate function formed by a linear combination of the output property f(t) of the magnetic sensor 1, the magnetic gradient components $g_x(t)$, $g_y(t)$ and the offset component d. Then, the optimum coefficients are obtained by the least squares method so that the sum of squares j of the difference between the approximate function and the actual observed quantity $O_i(t)$ is to be minimized.

That is, the sum of squares j is obtained by the following equation.

$$j = \sum_t^m \{O_i(t) - (af(t) + bg_x(t) + cg_y(t) + d)\}^2 \quad (5\text{-}8)$$

Here, m represents the number of samplings used for obtaining the sum of squares. The noise estimating circuit 135 substitutes m pieces of measurement data acquired m times in a predetermined sampling period into the equation (5-8) to obtain the sum of squares.

Next, a combination of the coefficients "a", "b", "c" and "d" which gives the minimum value of the sum of squares j is calculated under the following conditions.

$$\frac{\partial j}{\partial a} = \frac{\partial j}{\partial b} = \frac{\partial j}{\partial c} = \frac{\partial j}{\partial d} = 0 \quad (5\text{-}9)$$

Specifically, the coefficients a, b, c, and d are obtained by solving the following simultaneous equations.

$$\begin{pmatrix} \sum f^2(t) & \sum f(t)g_x(t) & \sum f(t)g_y(t) & \sum f(t) \\ \sum f(t)g_x(t) & \sum g_x^2(t) & \sum g_x(t)g_y(t) & \sum g_x(t) \\ \sum f(t)g_x(t) & \sum g_x(t)g_y(t) & \sum g_y^2(t) & \sum g_y(t) \\ \sum f(t) & \sum g_x(t) & \sum g_y(t) & n \end{pmatrix} \begin{pmatrix} a \\ b \\ c \\ d \end{pmatrix} = \begin{pmatrix} \sum O_i(t)f(t) \\ \sum O_i(t)g_x(t) \\ \sum O_i(t)g_y(t) \\ \sum O_i(t) \end{pmatrix} \quad (5\text{-}10)$$

The noise estimating circuit 135 calculates the coefficients "a", "b", "c", and "d" by substituting the actual observed quantity $O_i(t)$ into the calculation equation previously obtained by solving the above simultaneous equations.

Next, the noise removing unit 132 obtains the magnetic signal $S_i(t)$ from the object by removing the noise component from the actual observed quantity $O_i(t)$ as follows.

$$S_i(t) = D_i(t) - (af(t) + bg_x(t) + cg_y(t) + d) \quad (5\text{-}11)$$

As described above, according to the magnetic field measurement apparatus 50 and the magnetic field measurement method of the present embodiment, it is possible to remove the influence of the output properties of the magnetic sensor group 11 even in the case where the external magnetic field is inclined.

Sixth Embodiment

Figure 18:
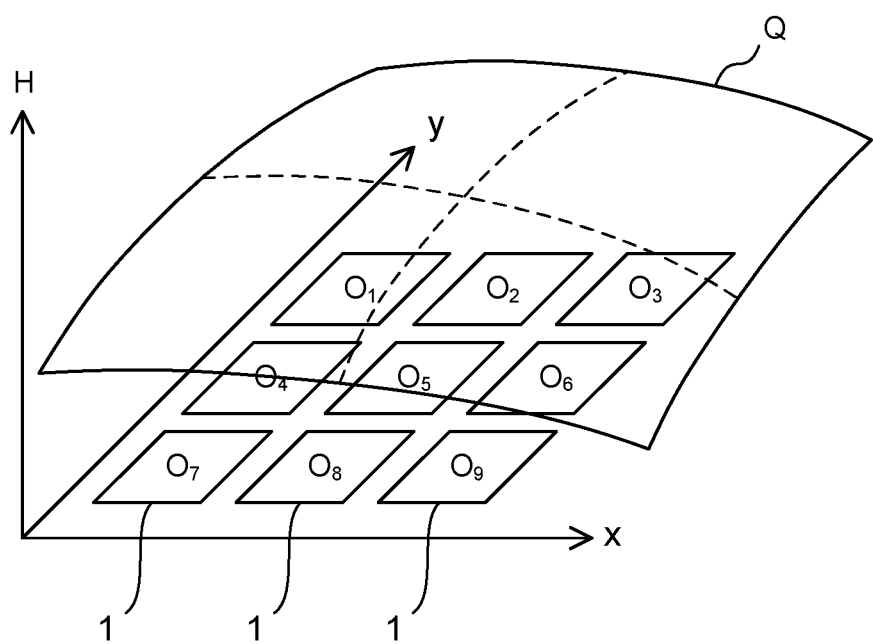
FIG. 18 is a diagram illustrating a distribution of an external magnetic field that can be removed in a sixth embodiment.

FIG. 18 illustrates an external magnetic field distribution that can be removed in the sixth embodiment.

In the present embodiment, as illustrated in FIG. 18, the noise is removed in such a way that the distribution of the intensity of the external magnetic field in the attachment portion of the magnetic sensor group 11 is approximated to the parabolic surface Q.

In urban areas where there are many magnetic noise sources, such curved magnetic field distribution is expected to occur. This embodiment is effective to remove noise in magnetic field measurement in such an urban noise environment.

Note that the noise cancellation of this embodiment can be performed by the magnetic field measurement apparatus 50 illustrated in FIG. 16.

In the present embodiment, the distribution in the spatial direction of the magnetic field noise component is expressed by a function of a paraboloid. The variables of the parabolic function are found by the least squares approximation of the function to the observed quantity to thereby obtain the spatial distribution of the magnetic noise component.

First, the model function of the magnetic noise component is approximated as follows.

$$N(x,y)=d_1x^2+d_2x+d_3y^2+d_4y+d_5 \quad (6\text{-}1)$$

It should be noted that the model function is not limited to the above-described one, but may be approximated as follows.

$$N(x,y)=d_1x^2+d_2x+d_3y^2+d_4y+d_5xy+d_6 \quad (6\text{-}2)$$

In the following explanation, the case approximated by the equation (6-2) will be described as an example.

The observed quantity at the latest sampling is expressed as O (x, y).

Here, it is assumed that the magnetic sensor group 11 includes n magnetic sensors. $(x_i, y_i)$ represents the position coordinates of the magnetic sensor 1 of the i-th channel. O $(x_i, y_i)$ represents the observed quantity of the magnetic sensor 1 of i-th channel.

Next, a combination of variables $d_1$ to $d_5$ that satisfies the condition of minimizing the error between this observed quantity O $(x_i, y_i)$ and the model function.

The error evaluation function E of the observed quantity and the model function is expressed as the sum of the squares of the difference between the observed quantity and the value of the model function at that position as follows.

$$E = \sum_{i=1}^{n} \{O(x_i, y_i) - N(x_i, y_i)\}^2 \quad (6\text{-}3)$$

The minimum value of the error evaluation function E is obtained by the following condition.

$$\frac{\partial E}{\partial d_1} = \frac{\partial E}{\partial d_2} = \frac{\partial E}{\partial d_3} = \frac{\partial E}{\partial d_4} = \frac{\partial E}{\partial d_5} = 0 \quad (6\text{-}4)$$

The above simultaneous equations are solved to find the unknown variables $d_1$ to $d_5$.

Here, if N $(x_i, y_i)$ in the equation (6-3) is written in the form of the equation (6-1), the error evaluation function E is expressed as follows.

$$E = \sum_{i=1}^{n} \{O(x_i, y_i) - d_1x_i^2 - d_2x_i - d_3y_i^2 - d_4y_i - d_5\}^2 \quad (6\text{-}5)$$

Therefore, the equation (6-4) is expressed as follows.

$$\begin{bmatrix} \sum_{i=1}^{n} x_i^4 & \sum_{i=1}^{n} x_i^3 & \sum_{i=1}^{n} x_i^2 y_i^2 & \sum_{i=1}^{n} x_i^2 y_i & \sum_{i=1}^{n} x_i^2 \\ \sum_{i=1}^{n} x_i^3 & \sum_{i=1}^{n} x_i^2 & \sum_{i=1}^{n} x_i y_i^2 & \sum_{i=1}^{n} x_i y_i & \sum_{i=1}^{n} x_i \\ \sum_{i=1}^{n} x_i^2 y_i^2 & \sum_{i=1}^{n} x_i y_i^2 & \sum_{i=1}^{n} y_i^4 & \sum_{i=1}^{n} y_i^3 & \sum_{i=1}^{n} y_i^2 \\ \sum_{i=1}^{n} x_i^2 y_i & \sum_{i=1}^{n} x_i y_i & \sum_{i=1}^{n} y_i^3 & \sum_{i=1}^{n} y_i^2 & \sum_{i=1}^{n} y_i \\ \sum_{i=1}^{n} x_i^2 & \sum_{i=1}^{n} x_i & \sum_{i=1}^{n} y_i^2 & \sum_{i=1}^{n} y_i & n \end{bmatrix} \begin{bmatrix} d_1 \\ d_2 \\ d_3 \\ d_4 \\ d_5 \end{bmatrix} = \quad (6\text{-}6)$$

$$\begin{bmatrix} \sum_{i=1}^{n} x_i^2 O(x_i, y_i) \\ \sum_{i=1}^{n} x_i O(x_i, y_i) \\ \sum_{i=1}^{n} y_i^2 O(x_i, y_i) \\ \sum_{i=1}^{n} y_i O(x_i, y_i) \\ \sum_{i=1}^{n} O(x_i, y_i) \end{bmatrix}$$

In the matrix of 5 rows and 5 columns on the left side of the above equation, $X_i$, $Y_i$ correspond to the coordinates of the i-th channel and are fixed in advance, so that the computation is easy and the inverse matrix can also be obtained. Therefore, it is possible to calculate the variables $d_1$ to $d_5$ by using the magnetic gradient calculating unit 136 of the signal processing unit 53 of the magnetic field measurement apparatus 50 shown in FIG. 16.

As a result, the gradient of the external magnetic field noise component is obtained. Subsequently, by subtracting the estimated noise component from the observed quantity, it is possible to obtain the measured quantity that is the magnetic field component from the object such as a living body.

According to the present embodiment, it is possible to estimate noise in the case where there is a magnetic gradient with a curvature across the channels on the magnetic sensor group 11.

The parabolic approximation as in the present embodiment achieves a higher reduction ratio of magnetic noise components than the plane approximation described in the third and fourth embodiments.

Also in the present embodiment, the removal of the non-correlated component as described in the second embodiment can be applied to the above noise component.

Seventh Embodiment

In the fourth embodiment, multiple pieces of measurement data are acquired in the time axis direction, and the noise component is estimated based on the correlation among the pieces of measurement data. Based on the same concept as this, multiple pieces of measurement data may be acquired from points discrete in the spatial direction, and can be used for noise removal by estimating a noise component in a different calculation method based on a correlation among the multiple pieces of measurement data.

To this end, in the seventh embodiment, a noise elimination method based on the correlation among the measurement data of the magnetic sensors 1 of the magnetic sensor group 11 will be described.

Figure 19:
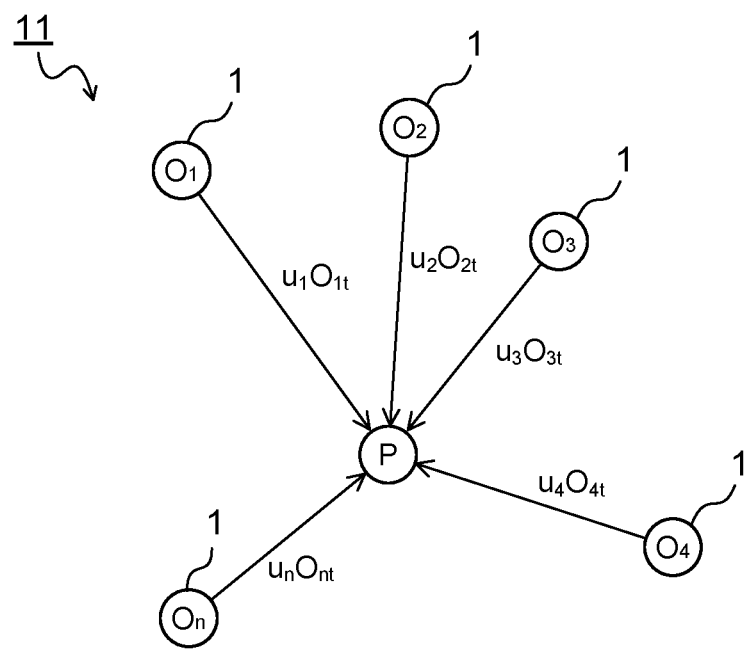
FIG. 19 is a diagram illustrating a method of obtaining a correlation between channels in a seventh embodiment.

FIG. 19 is a diagram illustrating a method of obtaining a spatial correlation in the present embodiment.

In the example of FIG. 19, the magnetic sensor group 11 includes n+1 magnetic sensors 1. Here, $O_{pt}$ represents the observed quantity at the time t of the magnetic sensor 1 of a P-th channel of interest. The observed quantities at the time t of the magnetic sensors 1 of the other channels are represented by $O_{1t}$ to $O_{nt}$. In this embodiment, it is considered that the intensity of the magnetic noise component of the magnetic sensor 1 of a P-th channel is represented by a linear combination of the products of coefficients $u_1$ to $u_n$ and the respective observed quantities $O_1$ to $O_n$ of the other channels. Here, the coefficients $u_1$ to $u_n$ are coefficients each depending on the distance from the magnetic sensor 1 of the P-th channel to the corresponding other magnetic sensor 1.

That is, the estimated value of the magnetic field noise component entering the P-th channel at the time t is denoted by $F_{pt}$ and is defined by the following equation.

$$F_{pt} = \sum_{i=1}^{n} u_i O_{it} \tag{7-1}$$

Here, $u_i$ is an unknown variable representing the degree of influence of the observed quantity of the i-th channel on the noise component of the magnetic sensor 1 of the P-th channel.

Next, the variance of the error between the observed quantity $O_{pt}$ of the P-th channel and the estimated value $F_{pt}$ of the magnetic noise component is obtained from the square sum of the residues.

$$E = \sum_{t=0}^{m-1} (O_{pt} - F_{pt})^2 \tag{7-2}$$

Here, the variance is obtained by using the observed quantities $O_{pt}$ of the P-th channel acquired from m current and past samplings where $t=0$ to $m-1$, and the estimated values $F_{pt}$ of the magnetic noise component. The number of m may be equal to or greater than the number of variables $u_i$.

Then, $u_i$ which minimizes the value of E in the above equation (7-2) may be found. The equation (7-2) is transformed for the unknown variable $u_i$.

$$E = \sum_{t=0}^{m-1} (O_{pt} - F_{pt})^2 \tag{7-3}$$

$$= \sum_{t=0}^{m-1} \{(O_{pt} - F_{pt} + u_i O_{it}) - u_i O_{it}\}^2$$

$$= u_i^2 \sum_{t=0}^{m-1} O_{it}^2 - 2u_i \sum_{t=0}^{m-1} O_{it}(O_{pt} - F_{pt} + u_i O_{it}) +$$

$$\sum_{t=0}^{m-1} (O_{pt} - F_{pt} + u_i O_{it})^2$$

$$= A_i^2 u_i^2 - 2A_i B_i u_i + C_i \tag{7-4}$$

$$= (A_i u_i - B_i)^2 + C_i - B_i^2$$

From the equation (7-4), it can be seen that E is a parabola with respect to the unknown variable $u_i$ and is minimized at the axis of the parabola.

From the equation (7-3), the following relational equations are obtained.

$$A_i^2 = \sum_{t=0}^{m-1} O_{it}^2 \tag{7-5}$$

$$A_i B_i = \sum_{t=0}^{m-1} O_{it}(O_{pt} - F_{pt} + u_i O_{it}) \tag{7-6}$$

$$C_i = \sum_{t=0}^{m-1} (O_{pt} - F_{pt} + u_i O_{it})^2 \tag{7-7}$$

Provided that the value of the axis of the parabola is $u'_i$, the following equation can be derived from the equations (7-5), (7-6) and (7-7).

$$u'_i = \frac{B_i}{A_i} = \frac{A_i B_i}{A_i^2} = \frac{\sum_{t=0}^{m-1} O_{it}(O_{pt} - F_{pt} + u_i O_{it})}{\sum_{t=0}^{m-1} O_{it}^2} \tag{7-8}$$

$$= u_i + \frac{1}{\sum_{t=0}^{m-1} O_{it}^2} \cdot \sum_{t=0}^{m-1} O_{it}(O_{pt} - F_{pt}) \tag{7-9}$$

Based on the above equations, the unknown variable $u_i$ is obtained using the observed quantities of the multiple magnetic sensors 1, and an estimated value of the noise component of the magnetic sensor 1 of the P-th channel is found. The estimated value of this noise component can be calculated by the noise estimating circuit 135 of the magnetic field measurement apparatus 50 in FIG. 16.

Thereafter, the noise removing unit 132 subtracts the estimated value $F_p$ of the magnetic noise component from the observed quantity $O_p$, thereby obtaining the measured quantity $S_p$ after noise removal.

Also in the present embodiment, the process of removing a non-correlated component may be performed by taking a local average of the measured quantities S of the adjacent channels.

As described above, according to the present embodiment as well, it is possible to remove an external magnetic field noise component, and thus to detect a weak magnetic field signal from an object such as a living body.

Eighth Embodiment

In the present embodiment, an estimated value is calculated by extrapolating the observed quantities of channels on an outer side of the magnetic sensor group 11 actually performing the measurement. The estimated value is used as a common noise component commonly applied to the magnetic sensors 1 in place of the average value of the first to seventh embodiments.

Figure 20:
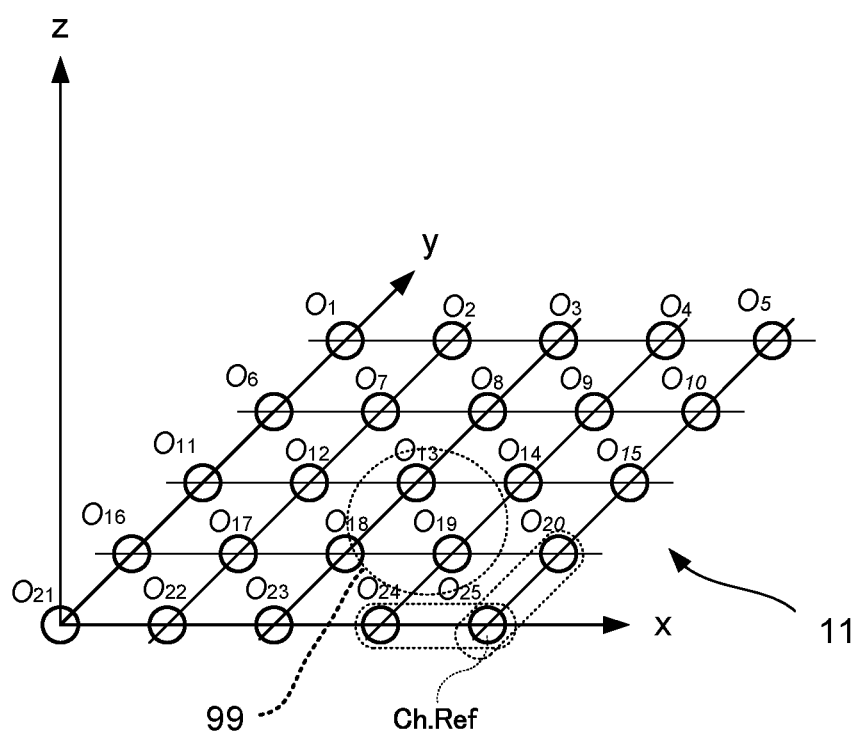
FIG. 20 is a diagram illustrating a method of obtaining an estimated value of the average value in an eighth embodiment.

FIG. 20 is a diagram illustrating a method of obtaining an estimated value of the average value in the present embodiment.

As illustrated in FIG. 20, the magnetic sensors 1 of the magnetic sensor group 11 are arranged in a lattice pattern in the X direction and the Y direction, and the magnetic sensors 1 at and around the center of the magnetic sensor group 11 is assumed to be attached to a portion above an object 99 (for example, the heart).

The magnetic field from the object 99 attenuates in inverse proportion to the square or cubic of the distance.

Therefore, if the magnetic sensor group 11 is sufficiently large with respect to the object 99, the magnetic field from the object 99 is not detected or very weak in the channel $O_{25}$ on the outer side of the magnetic sensor group 11.

Therefore, in the present embodiment, in FIG. 20, the observed quantities of the channels $O_{25}$ and $O_{20}$ are used to calculate an estimated value A at a position equidistant from the channel $O_{25}$ in the −y direction. This estimated value A is used as a common noise component commonly applied to the magnetic sensors 1 in place of the average value of all the magnetic sensors 1 in the noise removal of the first to seventh embodiments.

Further, in the present embodiment, the observed quantities of the channels $O_{25}$ and $O_{24}$ may be used to calculate an estimated value B at a position equidistant from the channel $O_{25}$ in the x direction.

In this case, the average value of the estimated values A and B is obtained and used instead of the average value of all the magnetic sensors 1.

The magnetic noise removal according to the present embodiment can be carried out using the magnetic field measurement apparatus 50 of FIG. 15. More specifically, the average value calculating unit 131 may acquire the observed quantities of the channels $O_{20}$, $O_{24}$, and $O_{25}$ and calculate the estimated values A and B and their average value based on the observed quantities.

Ninth Embodiment

In the above-described eighth embodiment, the reference channel is selected from the magnetic sensor group 11. However the present invention is not limited thereto, and the reference channel may be provided in addition to the magnetic sensors 1 of the magnetic sensor group 11.

Figure 21:
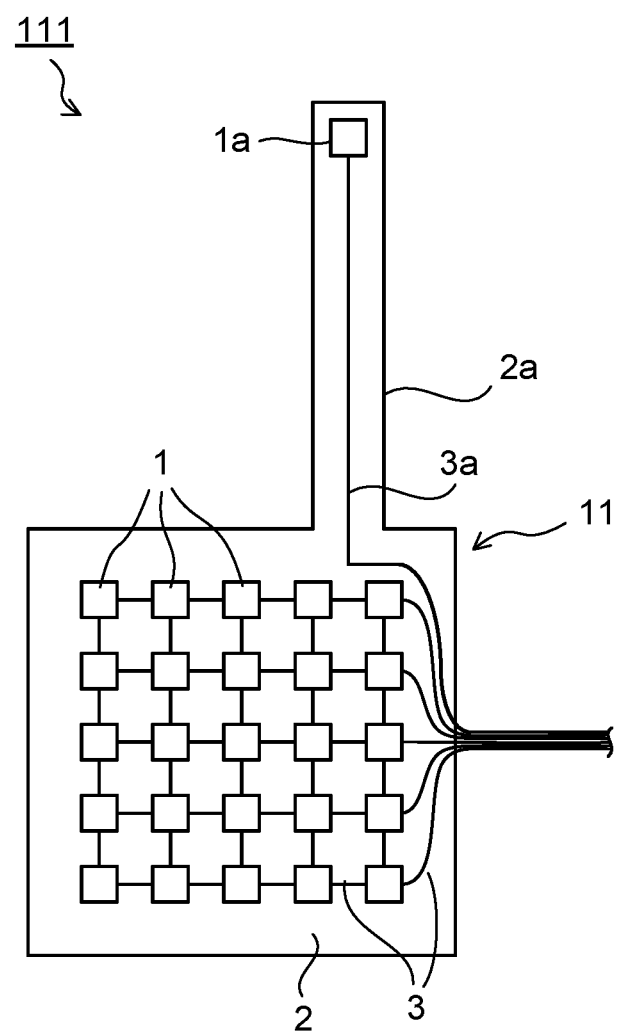
FIG. 21 is a plan view of a magnetic sensor unit according to a ninth embodiment.

FIG. 21 is a plan view of a magnetic sensor unit 111 of a magnetic field measurement apparatus according to the ninth embodiment. Since the configuration of the magnetic field measurement apparatus is similar to that of a magnetic field measurement apparatus 70 illustrated in FIG. 24, and the description thereof will be omitted.

As illustrated in FIG. 21, the magnetic sensor unit 111 of present embodiment is different from the magnetic sensor group 11, in that a reference magnetic sensor 1a is provided in addition to the magnetic sensors 1 arranged in the lattice pattern.

A support member 2 of the magnetic sensor unit 111 includes a protruding portion 2a extending from one side of the magnetic sensor group 11. A reference magnetic sensor 1a is provided at the tip of the protruding portion 2a. A wiring 3a is a wiring formed on the support member 2 and the protruding portion 2a. One end of the wiring 3a is connected to the reference magnetic sensor 1a. The reference magnetic sensor 1a is connected to the input circuit 12 of the magnetic field measurement apparatus 70 via the wiring 3a. The detection signal of the reference magnetic sensor 1a is input to the average value calculating unit 131 as the observed quantity of the reference channel.

In the magnetic sensor unit 111, the reference magnetic sensor 1a is provided at a position away from the magnetic sensor group 11. Thereby, the reference magnetic sensor 1a can be arranged at a position away from an object 98. This makes it possible to further reduce the magnetic field entering the reference magnetic sensor 1a from the object 98 and to further enhance the effect of noise removal.

Further, the magnetic field measurement apparatus can be made thinner by providing the reference magnetic sensor 1a on the support member 2 supporting the magnetic sensor group 11.

The installation position of the reference magnetic sensor 1a is not necessarily limited to the protruding portion 2a of the support member 2, but may be a separate module. The reference magnetic sensor 1 a may be disposed at any position as long as the position is sufficiently far from the object 98 to be measured by the magnetic sensor group 11.

Tenth Embodiment

Hereinafter, application examples of the magnetic field measurement apparatuses described in the above embodiments will be described. The following examples are not intended to limit the application range of the magnetic field measurement apparatuses described in the above embodiments. For the sake of convenience of explanation, an example using the magnetic field measurement apparatus 50 (see FIG. 16) will be described, but the other magnetic field measurement apparatuses 10, 20, 30, 40, and 70 described in the other embodiments may be used FIG. 22 is a diagram illustrating an application example of this embodiment in which the magnetic field measurement apparatus 50 is applied to a wearable sensor for measuring a cardiac magnetic field.

Figure 22:
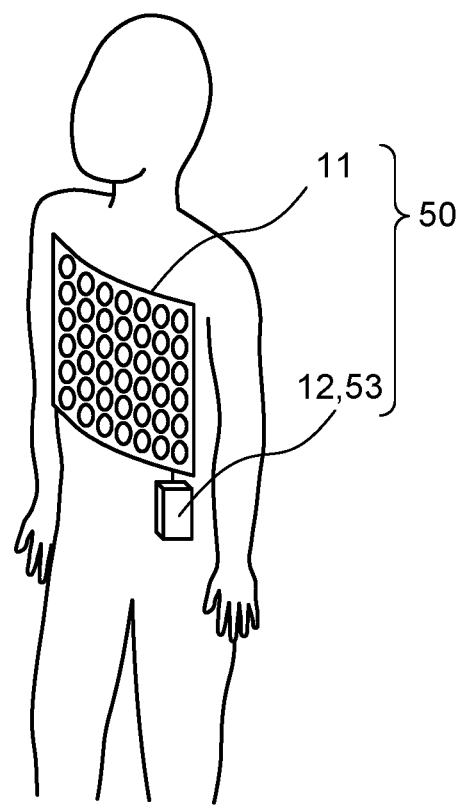
FIG. 22 is a diagram illustrating a method of measuring a cardiac magnetic field according to a tenth embodiment.

In the example illustrated in FIG. 22, the magnetic sensor group 11 mounted on a flexible sheet is attached onto the chest of a subject. When the magnetic sensor group 11 is attached in this manner, the magnetic sensor group 11 can detect the magnetic field from the nearby-located heart. That is, the magnetic sensors 1 of the magnetic sensor group 11 detect the magnetic field generated by myoelectricity transmitted through the muscles of the heart.

The observed signal of the magnetic sensor group 11 is input to the signal processing unit 53 via the input circuit 12. The signal processing unit 53 removes the noise components from the observed signal. Thereby, a detection signal of the weak cardiac magnetic field from each magnetic sensor 1 can be obtained.

Use of the detection signal of the cardiac magnetic field by the magnetic sensor group 11 enables not only detection of a heart rate, but also monitoring of movements of the muscles in the heart, which also enables detection of an abnormal movement of the heart which is a sign to a heart attack. Thus, the user can be informed of the sign to a heart attack, and may prevent the occurrence of the heart attack, for example, by resting the body.

It should be noted that the magnetic sensor group 11 for detecting the cardiac magnetic field is not limited to the wearable sensor.

For example, when installed in the bedding, the magnetic sensor group 11 can be used to detect the state of the heart rate during sleep.

The heart rate during sleep reflects the breathing state. When a subject falls into an apnea state for some reason during sleep, the heart rate increases. Therefore, the occurrence of sleep apnea syndrome can be examined by using the magnetic sensor group 11 installed in the bedding.

Eleventh Embodiment

Figure 23:
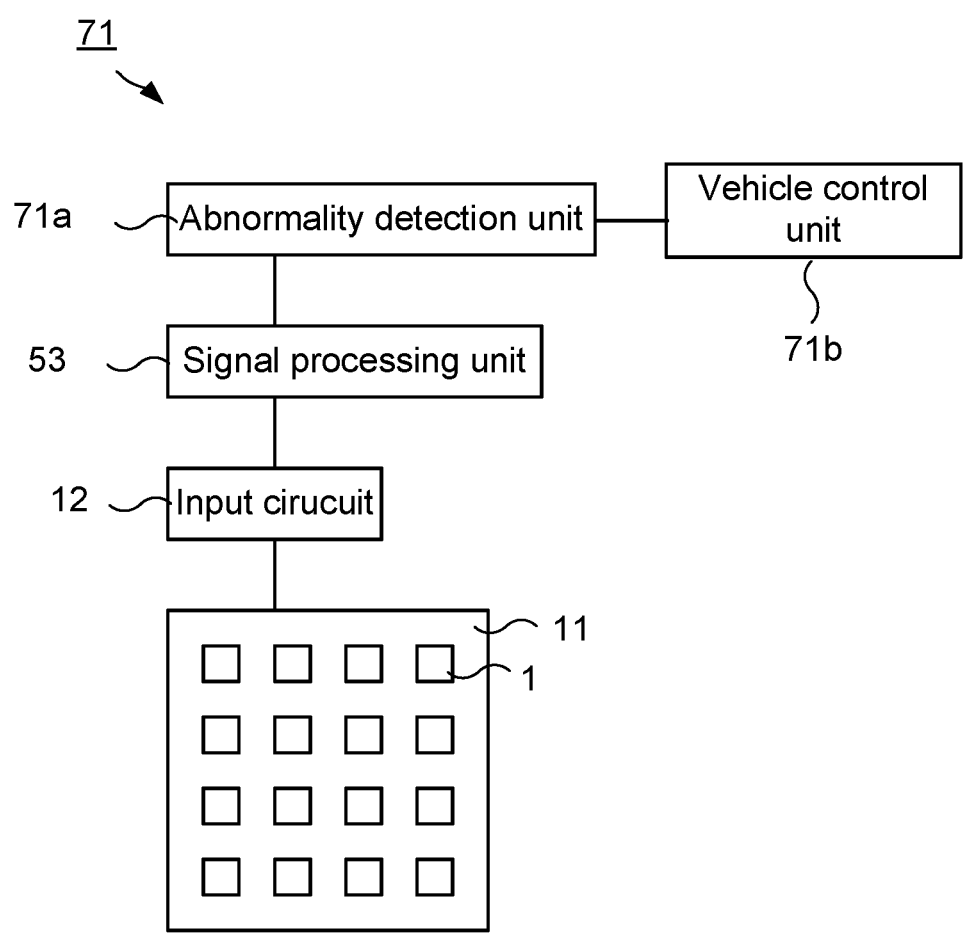
FIG. 23 is a block diagram of a vehicle operation control system according to an eleventh embodiment.

FIG. 23 is a diagram illustrating an application example of an eleventh embodiment in which the magnetic field measurement apparatus 50 is applied to a driving support system 71.

The driving support system 71 is configured to monitor the health conditions of a driver with the magnetic sensor group 11 attached to the body of the driver.

The signals from the magnetic sensors 1 are input to the signal processing unit 53 via the input circuit 12. The signal processing unit 53 removes the noise components and detects the heart rate, movement of the heart, or the like of the driver.

Data on the heart rate, movement of the heart, or the like of the driver output from the signal processing unit 53 is sent to an abnormality detection unit 71a. The abnormality detection unit 71a detects the health conditions of the driver such as an undesirable health condition or drowsiness which disturbs normal driving.

When detecting an abnormality of the driver, the abnormality detection unit 71a sends a signal to that effect to a vehicle control device 71b.

Based on the signal from the abnormality detection unit 71a, the vehicle control device 71b takes over the driving operation of the driver and performs control to park the vehicle in a safe place.

In this manner, when the driver becomes unable to drive due to a heart attack or the like, or when the driver cannot perform normal driving due to dozing, the driving support system 71 according to the present embodiment deprives the driver of the driving authority and switches to the automatic driving control to prevent an accident from occurring.

Twelfth Embodiment

Figure 24:
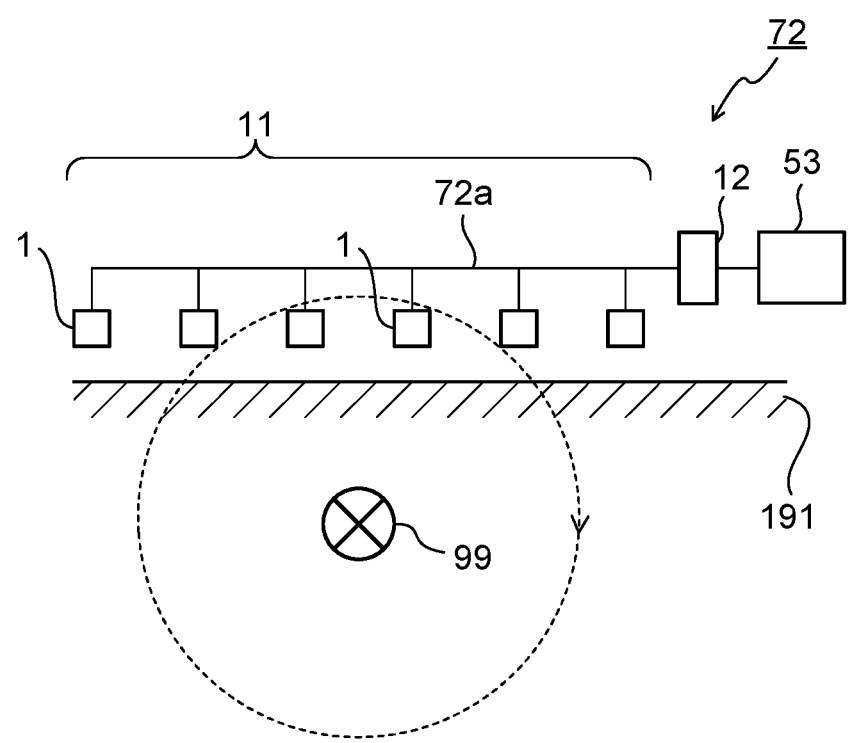
FIG. 24 is a block diagram of a magnetic field exploration system according to a twelfth embodiment.

FIG. 24 is a diagram illustrating an application example of a twelfth embodiment in which the magnetic field measurement apparatus 50 is applied to a magnetic field exploration system.

The size of the magnetic sensor group 11 (see FIG. 2) of the first embodiment is set to 20 cm square as an example, but the present invention is not limited thereto.

As illustrated in FIG. 24, a magnetic field exploration system 72 includes the magnetic sensor group 11, in which the interval between the magnetic sensors 1 is expanded to several tens cm to several meters. The magnetic sensor group 11 is expanded to a size of several meters square.

By using the magnetic field exploration system 72, it is possible to detect an object 99 under a ground surface 191. The object 99 is not limited to an underground magnetic body. For example, it is possible to investigate a flow path of groundwater, a leakage route of a power line, and so on.

In the case of the magnetic sensor group 11 in a large size as in the present embodiment, the function of the input circuit 12 may be incorporated into a peripheral circuit of the magnetic sensors 1. In this case, the signal processing unit 53 and the magnetic sensors 1 may be connected to each other by an optical line or a wireless communication system.

Thirteenth Embodiment

Figure 25A:
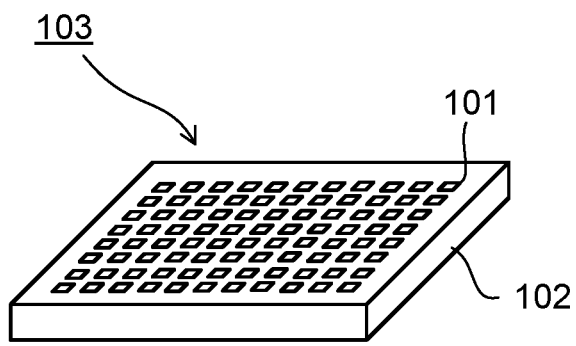
FIG. 25A is a perspective view of a magnetic probe according to a thirteenth embodiment, in which a magnetic sensor group is formed on a semiconductor chip.
Figure 25B:
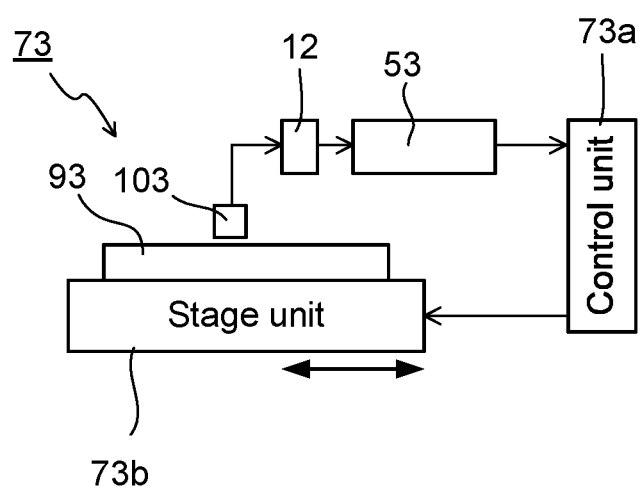
FIG. 25B is a block diagram of a magnetic microscope utilizing the magnetic probe of FIG. 25A.

FIG. 25A is a view illustrating an application example of a fifteenth embodiment in which a probe 103 is formed in which the magnetic sensor group 11 is integrated on a semiconductor substrate. FIG. 25B is a diagram illustrating an application example in which the magnetic sensor group, that is, the probe 103 of FIG. 25A is applied to a magnetic microscope.

As illustrated in FIG. 25A, in the present embodiment, magnetic sensors 101 are formed on a semiconductor substrate 102. The magnetic sensors 101 included in the magnetic sensor group (probe) 103 are manufactured by using microfabrication technology.

The size of the magnetic sensor group 11 on the probe 103 as described above depends on the degree of miniaturization of the magnetic sensor 101, and may be, for example, about 1 mm×1 mm.

As illustrated in FIG. 25B, a magnetic microscope 73 is obtained by using the probe 103 of FIG. 25A.

The magnetic microscope 73 includes a stage device 73b, and places and holds a sample 93 on the stage device 73b. The stage device 73b operates based on a control signal of a control unit 73a.

Above the stage device 73b, the probe 103 is arranged so as to face the sample 93. The signal of the probe 103 is input via the input circuit 12 to the signal processing unit 53 where noise is removed from the signal, and then is input to the control unit 73a.

The control unit 73a drives the stage device 73b so that the probe 103 scans the surface of the sample 93 and measures a local magnetic field. A magnetic image of the sample 93 is obtained by creating a distribution map of the magnetic field based on the position coordinates of the probe 103 and the intensity of the local magnetic field.

A conventional magnetic microscope is equipped with a SQUID (Superconducting Quantum Interferometer) probe or the like, but requires a large shield chamber made of a heavy and thick magnetic alloy. In addition, a cooling device is also required for cooling the SQUID element to the superconducting transition temperature or less. Accordingly, the device configuration becomes complicated and large.

In contrast to this, the magnetic microscope 73 of the present embodiment can operate the magnetic sensors 101 at room temperature and does not have to use a shield chamber since the ability to remove a magnetic noise of the external magnetic field is extremely high. Thus, the device configuration can be simplified.

In addition, having an excellent ability to measure a weak magnetic field, the probe 103 can be also used to observe nonmagnetic materials such as living bodies.

Fourteenth Embodiment

Figure 26:
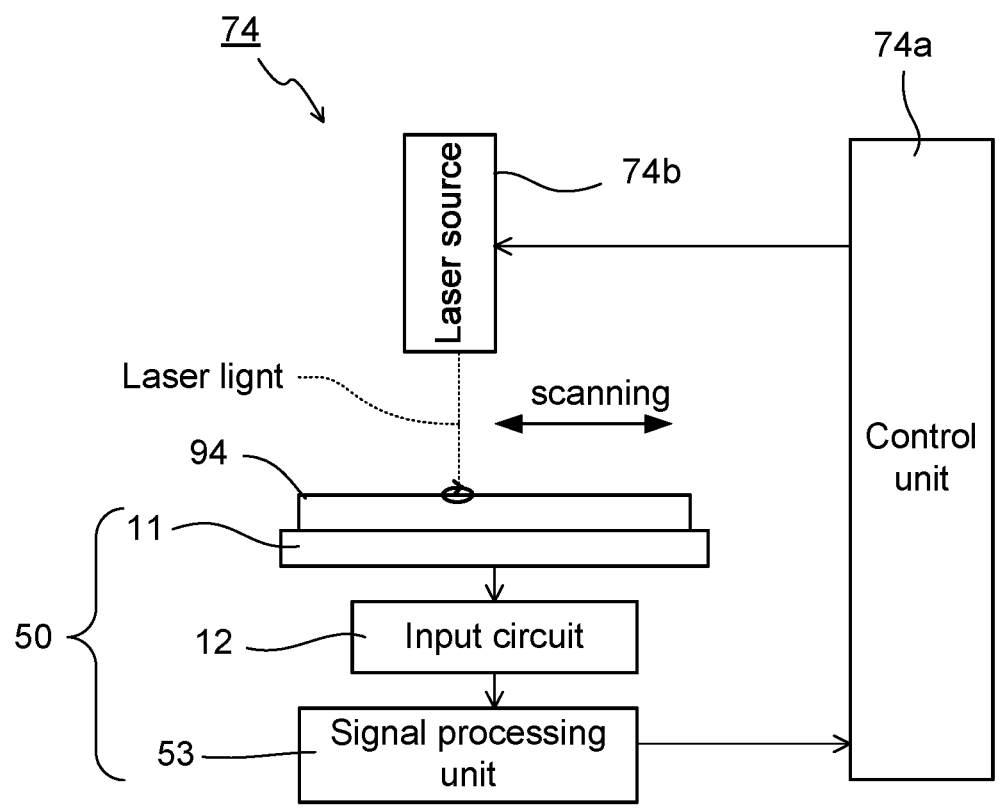
FIG. 26 is a block diagram of a semiconductor inspection apparatus according to a fourteenth embodiment.

FIG. 26 is a block diagram of a semiconductor inspection apparatus 74 according to a fourteenth embodiment.

As illustrated in FIG. 26, the semiconductor inspection apparatus 74 of the present embodiment places a semiconductor device 94 to be inspected on the magnetic sensor group 11. The semiconductor device 94 is irradiated with laser light emitted from a laser light source 74b.

When the semiconductor device 94 is irradiated with the laser light, electrons and holes are generated in the semiconductor device 94. If an irregular structure such as a pn junction or impurity concentration gradient exists within the range of diffusion length of electrons and holes, the carriers are separated and a local current flows to generate a magnetic field.

The magnetic field generated by the local current is detected by the magnetic sensors 1 included in the magnetic sensor group 11. The detection signal from the magnetic sensor group 11 is input to the signal processing unit 53 via the input circuit 12, and then is processed by the signal processing unit 53.

The magnetic field generated by the irradiation of the semiconductor device with laser light is weak, and detection of such weak magnetic field requires the SQUID conventionally. However, the semiconductor inspection apparatus 74 of the present embodiment includes the magnetic sensor group 11, the input circuit 12 and the signal processing unit 53, and thus is capable of detecting the magnetic field generated in the semiconductor because it has an excellent noise removal ability.

In the present embodiment, the semiconductor inspection apparatus 74 detects the intensity of the magnetic field generated from the semiconductor device 94 by means of the magnetic field measurement apparatus 50 while scanning the irradiation position of the laser light from the laser light source 74b under the control of the control unit 74a. Then, the semiconductor inspection apparatus 74 can obtain a two-dimensional image by mapping the coordinates of the irradiation position of the laser light and the intensity of the detected magnetic field.

This makes it possible to obtain information on the semiconductor device 94 such as defects and electrical characteristics.

In a conventional semiconductor inspection apparatus that detects a magnetic field by irradiation with a laser beam, a large shield chamber made of a heavy and thick magnetic alloy is required in order to reduce external magnetic noise. In addition, a cooling device is required to cool the SQUID for detecting a weak magnetic field to the superconducting transition temperature or less. Therefore, the device configuration becomes large, complicated and expensive.

On the other hand, according to the semiconductor inspection apparatus 74 of the present embodiment, the magnetic sensor group 11 can be operated at room temperature and the ability to remove magnetic noise of the external magnetic field is extremely high. Therefore, a shield chamber and a cooling device are unnecessary, and the device configuration can be simplified.

The invention claimed is:

1. A magnetic field measurement apparatus comprising:
    a magnetic sensor group including a plurality of magnetic sensors, each of the plurality of magnetic sensors being configured to detect an intensity of a magnetic field component from an object, the plurality of magnetic sensors configured such that a magnetic flux produced from the object passes through at least a first magnetic sensor and a magnetic flux returning to the object passes through at least a second magnetic sensor;
    an average value calculating unit configured to calculate a common noise component commonly applied to observed quantities of the magnetic sensors of all channels of the magnetic sensor group based on an arithmetic mean value of the observed quantities of the at least the first magnetic sensor and the second magnetic sensor so that a plus component of the magnetic flux at the first magnetic sensor and a minus component of the magnetic flux at the second magnetic sensor cancel out each other; and
    a noise removing unit configured to subtract the calculated common noise component obtained by the average value calculating unit as an estimated value of a magnetic noise component from the observed quantity of each of the magnetic sensors to remove an external magnetic noise component, and after removing the external magnetic noise component, detect a magnetic field from the object based on another average value of at least two of the plurality of magnetic sensors.

2. The magnetic field measurement apparatus according to claim 1, wherein the average value calculating unit calculates the common noise component by taking an arithmetic mean value of the observed quantities of the magnetic sensors of all the channels.

3. The magnetic field measurement apparatus according to claim 1, wherein the average value calculating unit calculates, as the common noise component, an estimated value obtained by extrapolating the observed quantities of the magnetic sensors of the channels located on an outer side of the magnetic sensor group.

4. The magnetic field measurement apparatus according to claim 1, further comprising a noise estimating circuit configured to calculate an estimated value of the magnetic noise component of each of the magnetic sensors by taking a correlation between the common noise component and the observed quantity of the magnetic sensor based on results of a plurality of measurements performed at different times.

5. The magnetic field measurement apparatus according to claim 4, wherein the noise estimating circuit calculates the estimated value of the magnetic noise component of the magnetic sensor of a channel of interest by taking a correlation between the observed quantity of the magnetic sensor of the channel of interest with the observed quantities of the magnetic sensors of the other channels based on results of a plurality of measurements performed at different times.

6. The magnetic field measurement apparatus according to claim 1, further comprising a common power source configured to drive the plurality of magnetic sensors included in the magnetic sensor group.

7. The magnetic field measurement apparatus according to claim 1, wherein the magnetic sensor group is configured to cover at least a part of the object.

8. The magnetic field measurement apparatus according to claim 1, wherein the average value calculating unit calculates, as the common noise component, an arithmetic mean value of the observed quantities of the magnetic sensors of all the channels.

9. A magnetic field measurement apparatus-comprising:
    a magnetic sensor group including a plurality of magnetic sensors;
    an average value calculating unit configured to calculate a common noise component commonly applied to observed quantities of the magnetic sensors of all channels of the magnetic sensor group;
    a noise removing unit configured to detect a magnetic field from an object by subtracting the common noise component obtained by the average value calculating unit as an estimated value of a magnetic noise component from the observed quantity of each of the magnetic sensors; and
    a magnetic gradient calculating unit configured to calculate a distribution of the magnetic noise components as an approximate function of the common noise component with position coordinates of the magnetic sensors, and calculate the estimated value of the magnetic noise component of each of the magnetic sensors based on the approximate function.

10. The magnetic field measurement apparatus according to claim 9, wherein the magnetic gradient calculating unit approximates the distribution of the magnetic noise components as a plane.

11. The magnetic field measurement apparatus according to claim 9, wherein the magnetic gradient calculating unit approximates the distribution of the magnetic noise components as a parabolic surface.

12. A magnetic field measurement apparatus comprising:
    a magnetic sensor group including a plurality of magnetic sensors;
    an average value calculating unit configured to calculate a common noise component commonly applied to observed quantities of the magnetic sensors of all channels of the magnetic sensor group;

a noise removing unit configured to detect a magnetic field from an object by subtracting the common noise component obtained by the average value calculating unit as an estimated value of a magnetic noise component from the observed quantity of each of the magnetic sensors; and a non-correlated component reduction unit configured to remove a non-correlated component by finding a local average value of the measured quantity of a magnetic sensor of interest and the measured quantity of a magnetic sensor adjacent to the magnetic sensor of interest.

13. A magnetic field measurement method comprising;

obtaining observed quantities from a plurality of magnetic sensors arranged near an object, each of the plurality of magnetic sensors being configured to detect an intensity of a magnetic field component from the object, the plurality of magnetic sensors configured such that a magnetic flux produced from the object passes through at least a first magnetic sensor and a magnetic flux returning to the object passes through at least a second magnetic sensor;

calculating a common noise component commonly applied to observed quantities of the plurality of magnetic sensors of all channels based on an arithmetic mean value of the observed quantities of the at least the first magnetic sensor and the second magnetic sensor so that a plus component of the magnetic flux at the first magnetic sensor and a minus component of the magnetic flux at the second magnetic sensor cancel out each other; and subtracting the calculated common noise component from the observed quantity of each of the magnetic sensors to remove an external magnetic noise component, and after removing the external magnetic noise component, detecting a magnetic field from the object based on another average value of at least two of the plurality of magnetic sensors.

14. The magnetic field measurement method according to claim 13, wherein the common noise component is calculated by taking an arithmetic mean value of the observed quantities of the magnetic sensors of all the channels.

15. The magnetic field measurement method according to claim 13, wherein as the common noise component, an estimated value is calculated by extrapolating the observed quantity of a magnetic sensor placed away from the object among the plurality of magnetic sensors.

16. The magnetic field measurement method according to claim 13, further comprising:

calculating an estimated value of a magnetic noise component of each of the magnetic sensors by taking a correlation between the common noise component and the observed quantity of the magnetic sensor based on results of a plurality of measurements performed at different times; and detecting a magnetic field from the object by subtracting the estimated value of the magnetic noise component from the observed quantity of the magnetic sensor.

17. The magnetic field measurement method according to claim 13, further comprising calculating an estimated value of a magnetic noise component of the magnetic sensor of a channel of interest by taking a correlation between the observed quantity of the magnetic sensor of the channel of interest with the observed quantities of the magnetic sensors of the other channels based on results of a plurality of measurements performed at different times.

18. A magnetic field measurement method comprising:

obtaining observed quantities from a plurality of magnetic sensors arranged near an object;

calculating a common noise component commonly applied to observed quantities of the plurality of magnetic sensors of all channels;

detecting a magnetic field from the object by subtracting the common noise component from the observed quantity of each of the magnetic sensors; and calculating a distribution of magnetic noise components of the magnetic sensors as an approximate function of the common noise component with the position coordinates of the magnetic sensors, and calculating an estimated value of the magnetic noise component of each of the magnetic sensors based on the approximate function.

19. The magnetic field measurement method according to claim 18, wherein the distribution of the magnetic noise components is approximated by a plane.

20. The magnetic field measurement method according to claim 18, wherein the distribution of the magnetic noise components is approximated by a parabolic surface.

21. A magnetic field measurement method comprising:

obtaining observed quantities from a plurality of magnetic sensors arranged near an object;

calculating a common noise component commonly applied to observed quantities of the plurality of magnetic sensors of all channels;

detecting a magnetic field from the object by subtracting the common noise component from the observed quantity of each of the magnetic sensors; and removing a non-correlated component by finding a local average value of the measured quantity of a magnetic sensor of interest and the measured quantity of a magnetic sensor adjacent to the magnetic sensor of interest.

* * * * *